(12) United States Patent
Tong et al.

(10) Patent No.: US 12,133,801 B2
(45) Date of Patent: *Nov. 5, 2024

(54) THREE-DIMENSIONAL POROUS STRUCTURES FOR BONE INGROWTH AND METHODS FOR PRODUCING

(71) Applicant: DePuy Ireland Unlimited Company, County Cork (IE)

(72) Inventors: Weidong Tong, Warsaw, IN (US); Andrew T. Rosenberger, Baltimore, MD (US); Robert J. Kane, Warsaw, IN (US); Bryan J. Smith, Ft. Wayne, IN (US); Luke C. Ice, Garrett, IN (US); Fionnán Aodhán McNamara, County Carlow (IE); Edward Patrick Kavanagh, County Cork (IE)

(73) Assignee: DePuy Ireland Unlimited Company, Ringaskiddy (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/055,539

(22) Filed: Nov. 15, 2022

(65) Prior Publication Data

US 2023/0071706 A1    Mar. 9, 2023

Related U.S. Application Data

(63) Continuation of application No. 17/028,022, filed on Sep. 22, 2020, now Pat. No. 11,517,438.

(Continued)

(51) Int. Cl.
*A61F 2/28* (2006.01)
*A61F 2/30* (2006.01)
(Continued)

(52) U.S. Cl.
CPC ............... *A61F 2/28* (2013.01); *B33Y 80/00* (2014.12); *A61F 2002/30151* (2013.01);
(Continued)

(58) Field of Classification Search
None
See application file for complete search history.

(56) References Cited

U.S. PATENT DOCUMENTS 3,970,301 A * 7/1976 Lehmann ............... E04H 15/18
                                                                428/542.6
4,038,703 A    8/1977 Bokros
(Continued)

FOREIGN PATENT DOCUMENTS

EP        1800700 A2    6/2007
EP        2319462 A1    5/2011
(Continued)

OTHER PUBLICATIONS

Bobyn et al, Characteristics of bone ingrowth and interface mechanics of a new porous tantalum biomaterial; The Journal of Bone & Joint Surgery, vol. 81-B, No. 5, Sep. 1999, 907-914.
(Continued)

*Primary Examiner* — Ann Schillinger
(74) *Attorney, Agent, or Firm* — BakerHostetler

(57) ABSTRACT

An orthopaedic prosthetic component is provided. The orthopaedic prosthetic component comprises a porous three-dimensional structure shaped to be implanted in a patient's body. The porous three-dimensional structure comprises a plurality of unit cells. At least one unit cell comprises a first geometric structure having a first geometry and comprising a plurality of first struts, and a second geometric structure having a second geometry and comprising a plurality of second struts connected to a number of the plurality of first struts to form the second geometric structure.

18 Claims, 10 Drawing Sheets

Related U.S. Application Data

(60) Provisional application No. 62/906,004, filed on Sep. 25, 2019.

(51) Int. Cl.
*A61F 2/38* (2006.01)
*B33Y 80/00* (2015.01)

(52) U.S. Cl.
CPC .............. *A61F 2002/30158* (2013.01); *A61F 2002/3028* (2013.01); *A61F 2002/30535* (2013.01)

(56) References Cited

U.S. PATENT DOCUMENTS

| | | | |
|---|---|---|---|
| 4,479,271 A | 10/1984 | Bolesky et al. | |
| 4,795,472 A | 1/1989 | Crowninshield et al. | |
| 4,842,517 A | 6/1989 | Kawahara et al. | |
| 4,938,769 A | 7/1990 | Shaw | |
| 4,997,445 A | 3/1991 | Hodorek | |
| 5,007,220 A * | 4/1991 | Lalvani | E04B 1/32 403/174 |
| 5,265,395 A * | 11/1993 | Lalvani | E04B 1/32 403/176 |
| 5,387,243 A | 2/1995 | Devanathan | |
| 5,505,035 A * | 4/1996 | Lalvani | B64G 99/00 52/311.2 |
| 5,534,030 A | 7/1996 | Navarro et al. | |
| 5,534,032 A | 7/1996 | Hodorek | |
| 5,609,641 A | 3/1997 | Johnson et al. | |
| 5,702,484 A | 12/1997 | Goymann et al. | |
| 5,716,358 A | 2/1998 | Ochoa et al. | |
| 5,723,011 A | 3/1998 | Devanathan et al. | |
| 6,027,682 A | 2/2000 | Almquist et al. | |
| 6,080,219 A | 6/2000 | Jha et al. | |
| 6,206,924 B1 * | 3/2001 | Timm | A61F 2/28 623/17.11 |
| 6,520,997 B1 | 2/2003 | Pekkarinen et al. | |
| 6,641,616 B1 * | 11/2003 | Grundei | A61F 2/36 623/23.26 |
| 6,702,848 B1 * | 3/2004 | Zilla | A61F 2/06 623/1.39 |
| 6,869,448 B2 | 3/2005 | Tuke et al. | |
| 6,931,812 B1 * | 8/2005 | Lipscomb | E04B 1/19 52/653.1 |
| 6,993,406 B1 | 1/2006 | Cesarano, III et al. | |
| 7,226,245 B2 * | 6/2007 | Kent | B28B 7/0044 405/35 |
| 7,497,876 B2 * | 3/2009 | Tuke | A61F 2/30907 623/23.29 |
| 7,537,664 B2 | 5/2009 | O'Neill et al. | |
| 7,597,715 B2 | 10/2009 | Brown et al. | |
| 7,855,062 B2 * | 12/2010 | Harlow | A61P 19/08 424/463 |
| 8,021,432 B2 | 9/2011 | Meridew et al. | |
| 8,266,780 B2 | 9/2012 | Bollinger et al. | |
| 8,268,099 B2 | 9/2012 | O'Neill et al. | |
| 8,268,100 B2 | 9/2012 | O'Neill et al. | |
| 8,418,730 B2 * | 4/2013 | Kang | E04B 1/19 140/92.4 |
| 8,430,930 B2 * | 4/2013 | Hunt | A61F 2/40 623/17.11 |
| 8,470,047 B2 | 6/2013 | Hazebrouck et al. | |
| 8,556,981 B2 | 10/2013 | Jones et al. | |
| 8,562,348 B2 | 10/2013 | Collins et al. | |
| 8,590,157 B2 | 11/2013 | Kruth et al. | |
| 8,697,231 B2 * | 4/2014 | Longepied | A61F 2/28 428/316.6 |
| 8,826,602 B1 * | 9/2014 | Lipscomb | E04B 1/19 52/80.2 |
| 8,888,862 B2 | 11/2014 | Mcdonnell et al. | |
| 8,992,703 B2 | 3/2015 | O'Neill et al. | |
| 9,180,010 B2 | 11/2015 | Dong et al. | |
| 9,364,896 B2 * | 6/2016 | Christensen | B22F 3/11 |
| 9,456,901 B2 * | 10/2016 | Jones | C23C 4/02 |
| 9,636,226 B2 * | 5/2017 | Hunt | A61F 2/4611 |
| 10,307,260 B2 | 6/2019 | Heldreth et al. | |
| 10,399,147 B2 | 9/2019 | Scott et al. | |
| 10,517,737 B2 * | 12/2019 | Adams | A61F 2/4202 |
| 10,588,749 B2 * | 3/2020 | Sharp | B33Y 70/10 |
| 10,596,660 B2 | 3/2020 | Mccarthy et al. | |
| 10,688,726 B2 * | 6/2020 | Shidid | B29C 64/393 |
| 10,799,363 B2 * | 10/2020 | Pasini | B22F 10/00 |
| 10,940,015 B2 * | 3/2021 | Sack | A61F 2/4455 |
| 11,364,123 B2 * | 6/2022 | Tong | A61F 2/30771 |
| 11,517,438 B2 * | 12/2022 | Tong | A61F 2/389 |
| 2002/0120344 A1 | 8/2002 | Meulink et al. | |
| 2003/0180171 A1 | 9/2003 | Artz et al. | |
| 2004/0158999 A1 | 8/2004 | Trantow | |
| 2004/0236430 A1 | 11/2004 | Koch et al. | |
| 2006/0241776 A1 * | 10/2006 | Brown | A61B 17/7225 623/22.32 |
| 2009/0216325 A1 | 8/2009 | May et al. | |
| 2010/0174377 A1 * | 7/2010 | Heuer | A61L 27/30 435/395 |
| 2010/0191345 A1 | 7/2010 | Pressacco et al. | |
| 2010/0291401 A1 * | 11/2010 | Medina | B23K 26/32 219/121.66 |
| 2010/0298947 A1 | 11/2010 | Unger | |
| 2011/0076316 A1 * | 3/2011 | Sivananthan | A61P 19/02 435/395 |
| 2011/0313532 A1 * | 12/2011 | Hunt | A61F 2/46 623/18.11 |
| 2012/0321878 A1 * | 12/2012 | Landon | A61L 27/56 264/497 |
| 2013/0172927 A1 | 7/2013 | Natarajan et al. | |
| 2013/0218282 A1 * | 8/2013 | Hunt | A61F 2/40 623/23.42 |
| 2013/0218284 A1 | 8/2013 | Eickmann et al. | |
| 2013/0325129 A1 * | 12/2013 | Huang | A61F 2/44 623/17.16 |
| 2014/0257507 A1 | 9/2014 | Wang et al. | |
| 2015/0012109 A1 * | 1/2015 | Moreau | A61F 2/30771 264/497 |
| 2016/0027425 A1 * | 1/2016 | Cook | F28D 7/0058 428/221 |
| 2016/0184103 A1 * | 6/2016 | Fonte | A61L 27/56 623/23.5 |
| 2017/0071747 A1 | 3/2017 | Shidid et al. | |
| 2017/0095337 A1 * | 4/2017 | Pasini | A61F 2/36 |
| 2017/0258606 A1 * | 9/2017 | Afzal | A61F 2/4465 |
| 2017/0266007 A1 | 9/2017 | Gelaude et al. | |
| 2017/0348114 A1 | 12/2017 | Jones et al. | |
| 2018/0228613 A1 * | 8/2018 | Jones | A61F 2/4455 |
| 2018/0280145 A1 | 10/2018 | Jones et al. | |
| 2018/0368981 A1 * | 12/2018 | Mattes | A61L 27/045 |
| 2019/0046322 A1 | 2/2019 | Moore et al. | |
| 2019/0151113 A1 | 5/2019 | Sack | |
| 2019/0290441 A1 | 9/2019 | Tong et al. | |
| 2019/0298525 A1 | 10/2019 | Wright et al. | |
| 2019/0298533 A1 | 10/2019 | Kane | |
| 2020/0036011 A1 | 1/2020 | Numata et al. | |
| 2020/0129670 A1 | 4/2020 | Landon et al. | |
| 2020/0276019 A1 * | 9/2020 | Shetty | B33Y 40/20 |
| 2021/0085466 A1 | 3/2021 | Tong | |
| 2022/0117742 A1 | 4/2022 | Tong et al. | |
| 2022/0323225 A1 | 10/2022 | Tong et al. | |

FOREIGN PATENT DOCUMENTS

| | | |
|---|---|---|
| EP | 2774580 | 9/2014 |
| JP | 2002-038201 A | 2/2002 |
| JP | 3184817 U | 7/2013 |
| JP | 2019-517372 A | 6/2019 |
| RU | 2207825 C1 | 7/2003 |
| RU | 2325191 C1 | 5/2008 |

(56) References Cited

FOREIGN PATENT DOCUMENTS

WO 96/23459 A1 8/1996
WO 2009/022911 A2 2/2009

OTHER PUBLICATIONS

Chua et al, Development of a Tissue Engineering Scaffold Structure Library for Rapid Prototyping. Part 1: Investigation and Classification, Int J Adv Manuf Technol, 2003, 21:291-301.
Chua et al, Development of a Tissue Engineering Scaffold Structure Library for Rapid Prototyping. Part 2: Parametric Library and Assembly Program, Int J Adv Manuf Technol, 2003, 21: 302-312.
Hong et al, A New Ti-5Ag Alloy for Customized Prostheses by Three-dimensional Printing (3DPtm), Research Reports, Biomaterials & Bioengineering, J Dent Res 80(3), 2001, 860-863.
Meiners et al, Direct Generation of Metal Parts and Tools by Selective Laser Powder Remelting (SLPR); Fraunhofer Institute for Laser Technology (ILT), 1999, 655-662.
Morgan et al, Direct Metal Laser Re-Melting (DMLR) of 316L Stainless Steel Powder, Part 1: Analysis of Thin Wall Structures, Research in Advanced Technologies Group, Faculty of Engineering, The University of Liverpool, UK, 2001, 276-282.
Morgan et al, Direct Metal Laser Re-Melting of 316L Stainless Steel Powder, Part 2: Analysis of Cubic Primitives, Research in Advanced Technologies Group, Faculty of Engineering, The University of Liverpool, UK, 2001, 283-295.
Morgan et al, Experimental investigation of nanosecond pulsed Nd:YAG laser re-melted pre-placed powder beds, Rapid Prototyping Journal, vol. 7, No. 3, 2001, 159-172.
Morgan et al, High density net shape components by direct laser re-melting of single-phase powders, Journal of Materials Science 37 (2002), 3093-3100.
Mullen et al, Selective Laster Melting: A Unit Cell Approach for the Manufacture of Porous, Titanium, Bone In-Growth Constructs, Suitable for Orthopedic Applications. II. Randomized Structures, Journal of Biomedical Materials Research Part B: Applied Biomaterials, Jan. 2010, 178-188.
Pogson et al, The production of copper parts using DMLR, Rapid Prototyping Journal, vol. 9, No. 5, 2003, 334-343.
Ramos et al, Mechanics of the Selective Laser Raster-Scanning Surface Interaction, Department of Mechanical and Metallurgical Engineering, Pontificia Universidad, Chile, Department of Mechanical Engineering, University of Texas at Austin, Aug. 2003, 559-572.
Williams et al, Selective Laser Sintering Part Strength as a Function of Andrew Number, Scan Rate and Spot Size, Clemson University, 1996, 10 pages.
Williams, et al., Advances in modeling the effects of selected parameters on the SLS process, Rapid Prototyping Journal, vol. 4, No. 2, 1998, 90-100.
Wysocki et al., Laser and Electron Beam Additive Manufacturing Methods of Fabricating Titanium Bone Implants, Applied Sciences, 7, 657, 2017, 20 pages.
Yang et al., the design of scaffolds for use in tissue engineering, Part II. Rapid prototyping techniques, Tissue engineering, Feb. 2002; vol. 8(1), 1-11.
Yang et al., The design of scaffolds for use in tissue engineering. Part I. Traditional factors, Tissue engineering, Dec. 2001; vol. 7(6), 679-689.
Non-final Rejection issued Jan. 20, 2022 in U.S. Appl. No. 17/028,022, filed Sep. 22, 2020, 14 pages.

\* cited by examiner (the Y-axis of length represents either pore size or minimum window opening)

THREE-DIMENSIONAL POROUS STRUCTURES FOR BONE INGROWTH AND METHODS FOR PRODUCING

CROSS-REFERENCE TO RELATED APPLICATIONS

This is a continuation of U.S. patent application Ser. No. 17/028,022 filed Sep. 22, 2020, which claims priority to U.S. Patent Application Ser. No. 62/906,004 filed Sep. 25, 2019, the disclosure of each of which is hereby incorporated by reference as if set forth in its entirety herein.

TECHNICAL FIELD

The embodiments disclosed herein are generally directed towards porous metal structures and methods for manufacturing them, and, more specifically, to porous metal structures in medical devices that have geometric lattice configurations suited to allow for exact control of porosity and pore size in a porous metal structure.

BACKGROUND

The embodiments disclosed herein are generally directed towards three-dimensional porous structures for bone ingrowth and methods for producing said structures.

The field of rapid prototyping and additive manufacturing has seen many advances over the years, particularly for rapid prototyping of articles such as prototype parts and mold dies. These advances have reduced fabrication cost and time, while increasing accuracy of the finished product, versus conventional machining processes, such as those where materials (e.g., metal) start as a block of material, and are consequently machined down to the finished product.

However, the main focus of rapid prototyping three-dimensional structures has been on increasing density of rapid prototyped structures. Examples of modern rapid prototyping/additive manufacturing techniques include sheet lamination, adhesion bonding, laser sintering (or selective laser sintering), laser melting (or selective laser sintering), photopolymerization, droplet deposition, stereolithography, 3D printing, fused deposition modeling, and 3D plotting. Particularly in the areas of selective laser sintering, selective laser melting and 3D printing, the improvement in the production of high density parts has made those techniques useful in designing and accurately producing articles such as highly dense metal parts.

In the past few years, some in the additive manufacturing field have attempted to create solutions that provide the mechanical strength, interconnected channel design, porosity and pore size in porous structures necessary for application in promoting mammalian cell growth and regeneration. However, the current methods and geometries have limited control over the pore size distribution, which exerts a strong influence on the ingrowth behavior of mammalian cells such as bone. Moreover, the current methods and geometries often fall short in producing porous structures having unit cell geometries with pore sizes and porosities simultaneously in the range believed to be beneficial for ingrowth while maintaining structural integrity during the manufacturing process (e.g., 3D printing). As a result, current unit cell geometric structures must either have a very large pore size or very low porosity. Furthermore, current methods and geometries generally prevent close correlation between a selected strut length and diameter of a unit cell, within a structure's geometry, and the resulting geometric features desired in the porous structure.

Current methods of manufacturing porous metal materials for bone ingrowth have limited control over the pore size distribution, which exerts a strong influence on the ingrowth behavior of bone. Better simultaneous control of the maximum pore size, minimum pore size, and porosity would enable better bone ingrowth. Additive manufacturing techniques conceptually enable production of lattice structures with perfect control over the geometry but are practically limited to the minimum outer strut diameter that the machine can build, and by the need for any lattice structure to be self-supporting. The minimum strut diameter for current 3D printers is approximately 200-250 microns, which means that many geometric structures must either have a very large pore size or very low porosity.

SUMMARY

According to one aspect of the disclosure, an implantable apparatus includes a porous three-dimensional structure shaped to be implanted in a patient's body. The porous three-dimensional structure includes a plurality of interconnected organic unit cells. Each organic unit cell includes a plurality of outer struts and a plurality of internal struts. Respective groups of three outer struts intersect so as to define a respective plurality of outer nodes. Each internal strut extends from a different respective one of the outer nodes, and the internal struts intersect so as to define an internal node. The plurality of outer nodes includes a first outer node defined by the intersection of a first group of three outer struts and a second outer node defined by the intersection of a second group of three outer struts. A shortest path along the struts from the first outer node to the second outer node includes only three intermediate outer nodes of the plurality of outer nodes. A straight imaginary line extends through the first outer node and the second outer node, and the internal node is offset from the straight imaginary line.

In one example, each of the outer struts has a constant thickness along an entirety of its length.

In another example, each of the internal struts has a constant thickness along an entirety of its length.

In another example, at least one of the outer struts is curved along its length.

In another example, at least one of the internal struts is curved along its length.

In another example, all of the outer struts extend from and to a respective pair of the outer nodes along respective lengths, and the lengths of at least some of the outer struts are different than each other.

In another example, at least one of the outer struts is bent.

In another example, all of the outer struts are substantially straight along entireties of their respective lengths.

In another example, the plurality of outer struts includes a longest outer strut and a shortest outer strut whose length is no less than approximately 60% of that of the longest outer strut.

In another example, the plurality of outer struts includes a longest outer strut and a shortest outer strut whose length is no less than approximately ⅓ of that of the longest outer strut.

In another example, at least one of the internal struts is bent.

In another example, all of the internal struts are substantially straight along entireties of their respective lengths.

In another example, the implantable apparatus has a porosity between about 50% and about 75%.

In another example, the implantable apparatus includes a number of pores defined by the unit cells, respectively, wherein less than 14.3 percent of the pores have a pore size less than 0.1 mm.

Fifty percent of the pores can have a pore size that ranges from approximately 0.2 mm to approximately 0.7 mm.

In another example, the outer struts cooperate to define a number of outer openings, the internal struts cooperate with a number of the outer struts to form number of internal openings, the porous three-dimensional structure defines window sizes defined as a diameter of a circle positioned in the corresponding outer openings and inner openings, such that each of the struts that defines the outer openings and inner openings, respectively, is positioned on a tangent line of the circle, and the implantable apparatus comprises a number of pores defined by the unit cells, respectively, the pores defining a ratio of their respective pore sizes to any of its window sizes that is in the range of 1.00 to 2.90.

In another example, the internal node is the only internal node of the porous three-dimensional structure that is internal with respect to the outer nodes.

In another example, all of the internal struts intersect at the internal node.

In another example, the implantable apparatus comprises an organic rhombic trigonal trapezohedron having a ductility greater than a corresponding geometric rhombic trigonal trapezohedron.

In another example, each organic unit cell defines a first half and a second half separated from the first half by a plane that bisects the organic unit cell structure, and for all orientations of the plane, 1) at least some of the outer nodes of the first half of the organic unit cell structure are repositioned with respect to corresponding outer nodes a corresponding geometric unit cell structure in a first orientation, and 2) at least some of the outer nodes of the second half of the organic unit cell structure are repositioned with respect to corresponding outer nodes the corresponding geometric unit cell structure in second direction different than the first direction.

In another example, an orthopaedic implant includes the porous three-dimensional structure and a solid base, wherein the porous three-dimensional structure is attached to the solid base.

According to another aspect of the present disclosure, an implantable apparatus includes a porous three-dimensional structure that is shaped to be implanted in a patient's body. The porous three-dimensional structure including a plurality of interconnected organic unit cell structures. Each organic unit cell structure includes a plurality of outer struts. At least three outer struts of the plurality of outer struts intersect so as to define a respective plurality of outer nodes. The outer struts and nodes combine to substantially define a geometric structure that is within 50% of a geometric rhombic dodecahedron. The outer struts have a constant thickness along entireties of their respective lengths. The outer nodes include a first outer node and a second outer node opposite the first outer node so as to define a first pair of opposed nodes. The outer nodes further include a third outer node and a fourth outer node opposite the third outer node so as to define a second pair of opposed nodes. The outer nodes further include a fifth outer node and a sixth outer node opposite the fifth outer node so as to define a third pair of opposed nodes. All opposed outer nodes are separated from each other by three intermediate outer nodes of the plurality of outer nodes along a shortest path along the outer struts. A first straight imaginary line extends through the first outer node and the second outer node, a second straight imaginary line extends from the third outer node to the fourth outer node, and a third straight imaginary line that extends from the fifth outer node to the sixth outer node. The first and second straight imaginary lines intersect each other at a first intersection with respect to a select view of the porous three-dimensional structure, and the third straight imaginary line intersects the first straight imaginary line at a respective second intersection that is offset from the first intersection with respect to the select view of the porous three-dimensional structure.

In one example, each of the organic unit cell structures defines a first half and a second half separated from the first half by a plane that bisects the organic unit cell structure. For all orientations of the plane, 1) at least some of the outer nodes of the first half of the organic unit cell structure are repositioned with respect to corresponding outer nodes a corresponding geometric unit cell structure in a first orientation, and 2) at least some of the outer nodes of the second half of the organic unit cell structure are repositioned with respect to corresponding outer nodes the corresponding geometric unit cell structure in second direction different than the first direction In another example, the outer struts define a first geometric structure, and the porous three-dimensional structure further includes a plurality of internal struts that, in combination with the outer struts, define a plurality of second geometric structures inside the first geometry.

In another example, the plurality of internal struts consists of four internal struts that intersect each other so as to define an internal node.

In another example, the plurality of internal struts consists of eight internal struts, wherein all of the plurality of internal struts intersects at least one other one of the internal struts.

In another example, the implantable apparatus comprises an organic rhombic dodecahedron having a ductility greater than a corresponding geometric rhombic dodecahedron.

According to yet another aspect of the present disclosure, an implantable apparatus includes a porous three-dimensional structure shaped to be implanted in a patient's body. The porous three-dimensional structure includes a plurality of interconnected unit cells. Each unit cell includes a plurality of struts. At least three struts of the plurality of struts intersect so as to define a respective plurality of nodes, and at least one of the struts of the plurality of struts is bent along its length between a first node of the plurality of nodes to a second node of the plurality of nodes.

In one example, the struts define groups of three struts that intersect each other so as to define the first node and the second node.

According to another aspect, a porous three-dimensional structure is shaped to be implanted in a patient's body. The porous three-dimensional structure includes a plurality of interconnected unit cells. Each unit cell includes a plurality of struts. At least three struts of the plurality of struts intersect so as to define a respective plurality of nodes, and at least one of the struts of the plurality of struts is bent along its length between a first node of the plurality of nodes to a second node of the plurality of nodes.

In another example, an orthopaedic implant includes the porous three-dimensional structure and a solid base, wherein the porous three-dimensional structure is attached to the solid base.

BRIEF DESCRIPTION OF THE DRAWINGS

For a more complete understanding of the principles disclosed herein, and the advantages thereof, reference is now made to the following descriptions taken in conjunction with the accompanying drawings, in which.

DETAILED DESCRIPTION

Figure 1:
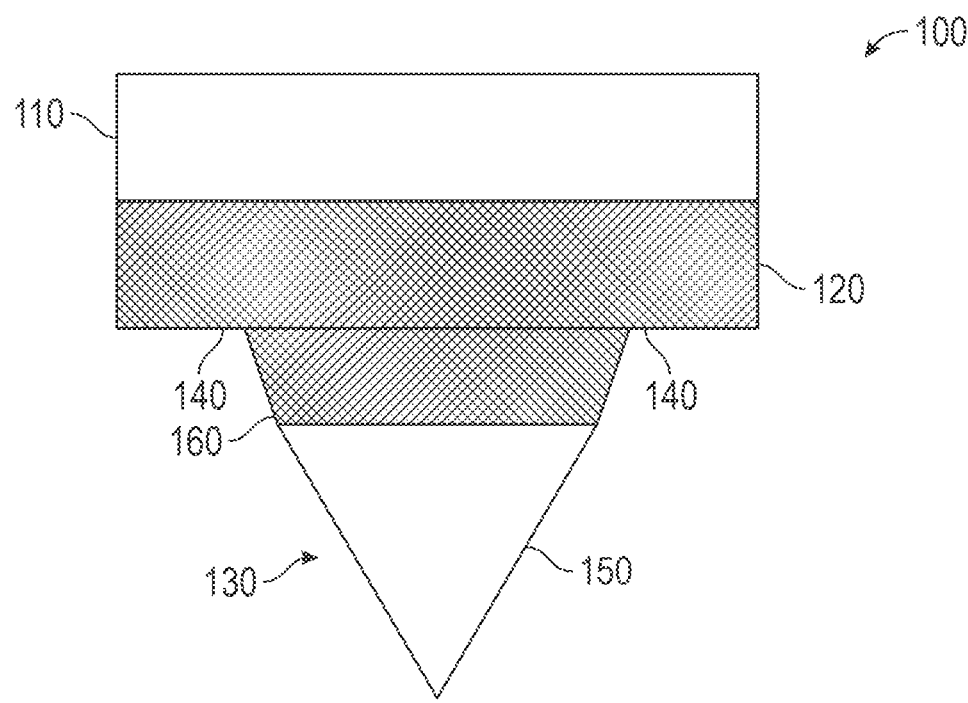
FIG. 1 is a simplified elevation view of an orthopaedic prosthetic component.

This specification describes exemplary embodiments and applications of the disclosure. The disclosure, however, is not limited to these exemplary embodiments and applications or to the manner in which the exemplary embodiments and applications operate or are described herein. Moreover, the FIGS. may show simplified or partial views, and the dimensions of elements in the FIGS. may be exaggerated or otherwise not in proportion. In addition, as the terms "on," "attached to," "connected to," "coupled to," or similar words are used herein, one element (e.g., a material, a layer, a base, etc.) can be "on," "attached to," "connected to," or "coupled to" another element regardless of whether the one element is directly on, attached to, connected to, or coupled to the other element, there are one or more intervening elements between the one element and the other element, or the two elements are integrated as a single piece. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

As used herein, "bonded to" or "bonding" denotes an attachment of metal to metal due to a variety of physicochemical mechanisms, including but not limited to: metallic bonding, electrostatic attraction and/or adhesion forces.

Unless otherwise defined, scientific and technical terms used in connection with the present teachings described herein shall have the meanings that are commonly understood by those of ordinary skill in the art.

The present disclosure relates to porous three-dimensional metallic structures and methods for manufacturing them for medical applications. As described in greater detail below, the porous metallic structures promote hard or soft tissue interlocks between prosthetic components implanted in a patient's body and the patient's surrounding hard or soft tissue. For example, when included on an orthopaedic prosthetic component configured to be implanted in a patient's body, the porous three-dimensional metallic structure can be used to provide a porous outer layer of the orthopaedic prosthetic component to form a bone in-growth structure. Alternatively, the porous three-dimensional metallic structure can be used as an implant with the required structural integrity to both fulfill the intended function of the implant and to provide interconnected porosity for tissue interlock (e.g., bone in-growth) with the surrounding tissue. In various embodiments, the types of metals that can be used to form the porous three-dimensional metallic structures can include, but are not limited to, titanium, titanium alloys, stainless steel, cobalt chrome alloys, tantalum or niobium.

Figure 2:
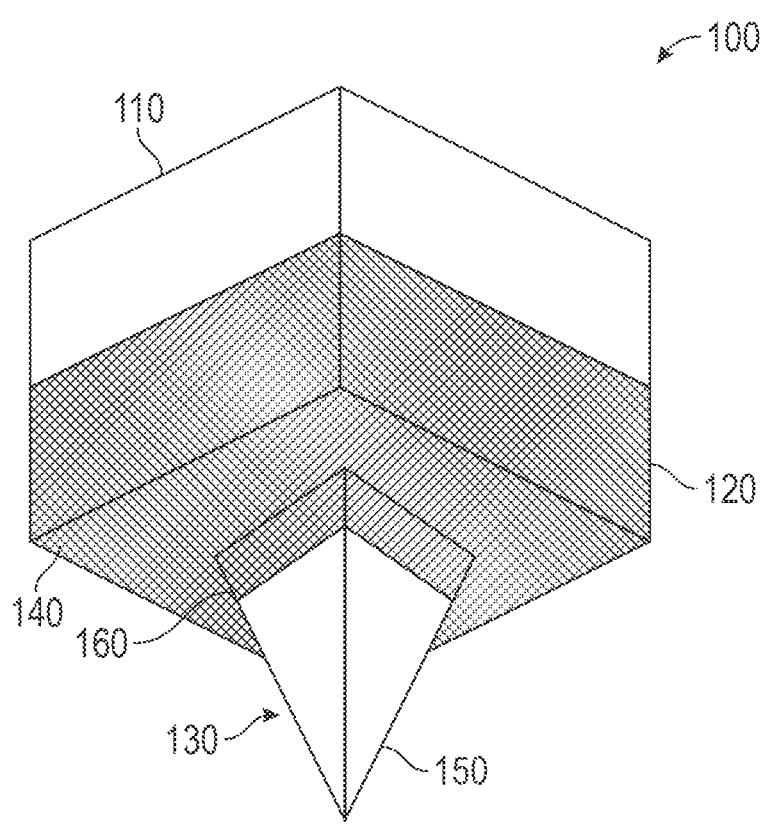
FIG. 2 is a simplified perspective view of the orthopaedic prosthetic component of FIG. 1.

Referring now to FIGS. 1 and 2, an implantable apparatus such as an orthopaedic implant or prosthetic component 100 is illustrated. The prosthetic component 100 includes a base 110, a porous three-dimensional structure or layer 120, and a cone or stem 130 extending away from the base 110. In the illustrative embodiment, the porous structure 120 surrounds a portion of the base 110 and a portion of the stem 130. It should be appreciated that the porous structure 120 can be provided as a layer separate from the base 110 and/or the stem 130. The porous structure 120 may also be provided as a coating that surrounds all of the base 110 and/or all of the stem 130. As described in greater detail below, the porous structure includes a plurality of unit cells that define voids or spaces that permit the ingrowth of bone, thereby promoting fixation of the prosthetic component 100 to a patient's bone.

The orthopaedic implant 100 may be implanted into a tibial bone. For example, the stem 130 can be inserted into the tibial bone, with a ledge portion 140 of implant 100 resting against a proximal portion of the tibial bone. It should be appreciated that the various porous structures described herein may be incorporated into various orthopaedic implant designs, including, for example, a tibial prosthetic component or a femoral prosthetic component similar to the tibial and femoral components shown in U.S. Pat. No. 8,470,047, which is expressly incorporated herein by reference. The porous structures may also be included in other orthopaedic implant designs, including a patella component shaped to engage a femoral prosthetic component and prosthetic components for use in a hip or shoulder arthroplasty surgery It should also be noted, for the preceding and going forward, that the base 110 can be any type of structure capable of, for example, contacting, supporting, connecting to or with, or anchoring to or with components of various embodiments herein. The base 110 can include, for example, a metal or non-metal tray, a metal or non-metal baseplate, a metal or non-metal structure that sits on a tray, and so on. The types of metal that can be used to form the base 110 include, but are not limited to, titanium, titanium alloys, stainless steel, cobalt chrome alloys, tantalum or niobium.

In the illustrative embodiment, the stem 130 includes a solid region 150, which is coated by a porous region 160 of the porous structure 120. The solid region 150 of the stem 130 is anchored to the base 110 and extends outwardly from the porous structure 120 such that the porous structure 120 surrounds the region of stem 130 proximal to base 110. In other embodiments, the stem 130 may be anchored to the porous structure 120. The types of metal that can be used to form the stem 130 include, but are not limited to, titanium, titanium alloys, stainless steel, cobalt chrome alloys, tantalum or niobium.

Figure 4:
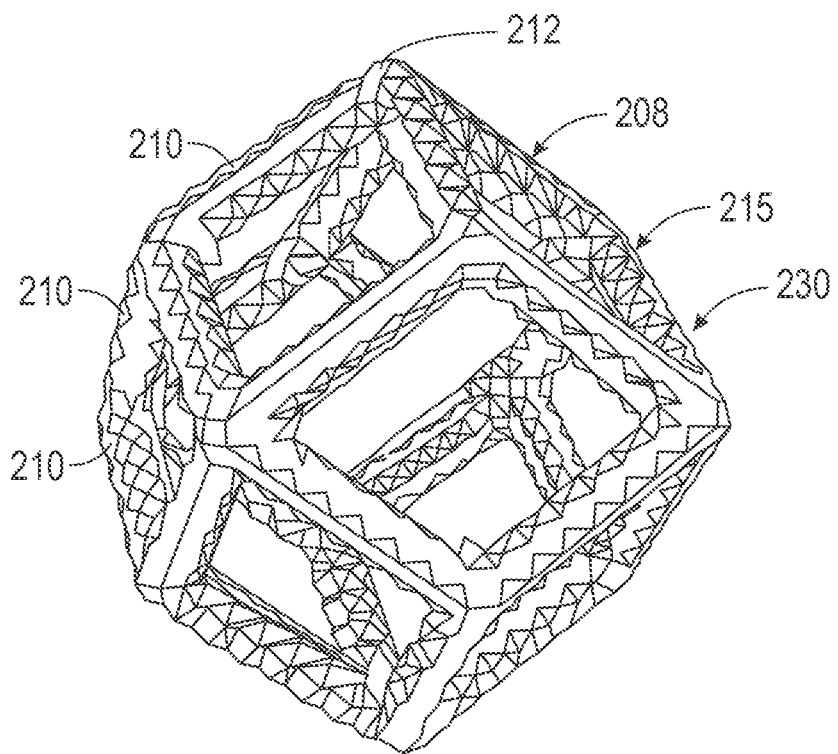
FIG. 4 is a perspective view of one geometric structure of the unit cell of FIG. 3.

Referring now to FIG. 4, the porous structure 120 of the implant 100 includes a plurality of connected unit cells, and at least some up to all of the unit cells illustratively have the geometric unit cell structure 200 shown in FIG. 4. The types of metal that can be used to form the unit cell structures shown in include, but are not limited to, titanium, titanium alloys, stainless steel, cobalt chrome alloys, tantalum or niobium. As shown in FIG. 4, each geometric unit cell structure includes a plurality of struts 208 that include a plurality of outer struts 210. The outer struts 210 combine to define a lattice structure. The outer struts 210 cooperate to form a geometric outer structure 230. In the illustrative embodiment, the outer geometry is a geometric rhombic dodecahedron 215. As described below with respect to FIGS. 12A-14C, the unit cells can include organic structures that differ from the geometric structures. In some examples, the organic structures are modified with respect to the geometric structures.

As used herein, the terms "substantial," "about," "approximate," words of similar import, and derivatives thereof when used with respect to a size, shape, dimension, direction, orientation, or the like include the stated size, shape, dimension, direction, orientation, or the like as well as a range associated with typical manufacturing tolerances, such as plus and minus 2%.

Referring to FIG. 4, the outer struts 210 further intersect each other so as to define a plurality of outer vertices or outer nodes 212. Respective groups of at least three of the outer struts 210 intersect each other so as to define a respective plurality of the outer nodes 212. For instance, each of the outer nodes 212 is defined by an intersection of three of the outer struts 210 in one example. Each of the outer struts 210 therefore extends from a respective first node of the outer nodes 212 to a respective second node of the outer nodes 212 along a respective length. Further, each of the plurality of outer nodes 212 has a position in three-dimensional space (e.g., along an x-direction, a y-direction, and a z-direction that are all oriented perpendicular to each other) with respect to the remaining outer nodes 212 of the plurality of outer nodes 212 that define the nodes 212 of the geometric rhombic dodecahedron 215. When the outer struts 210 define the geometric rhombic dodecahedron 215, the struts 210 combine to define fourteen outer nodes 212.

Figure 3:
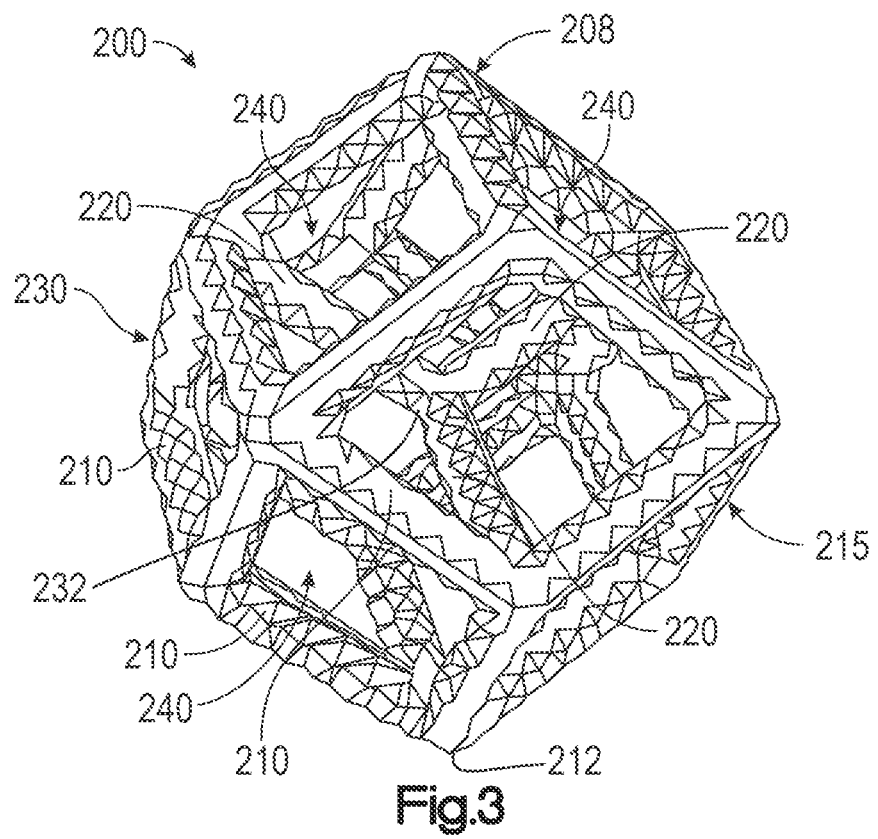
FIG. 3 is a perspective view of a unit cell of the porous structure of the orthopaedic prosthetic component of FIGS. 1-2.

As shown in FIG. 3, the struts 208 include a plurality of outer struts 210 and a plurality of internal struts 220. Thus, each geometric unit cell structure 200 illustrated in FIG. 3 includes a plurality of outer struts 210 and a plurality of internal struts 220, which form a first geometric structure 230 and a plurality of second geometric structures 240 that are within the first geometric structure 230. In the illustrative embodiment, the first geometric structure 230 comprises the plurality of outer struts 210. As described above with respect to FIG. 4, the plurality of outer struts 210 of FIG. 3 cooperate to form a geometric rhombic dodecahedron. Thus, the first geometric structure 230 defines a geometric rhombic dodecahedron. The internal struts 220 intersect each other so as to define an internal node 232. In the illustrated embodiment, all internal struts 220 intersect each other so as to define the internal node 232. In the illustrated embodiment, the internal struts 220 intersect each other so as to define only the single internal node 232 and no other internal nodes. At least some up to all of the connected unit cells of the porous structure 120 of the implant 100 can have the unit cell structure 200 shown in FIG. 3. Accordingly, the unit cell structure 200 defines only one single internal node 232 that is internal with respect to the outer nodes 212.

Figure 5:
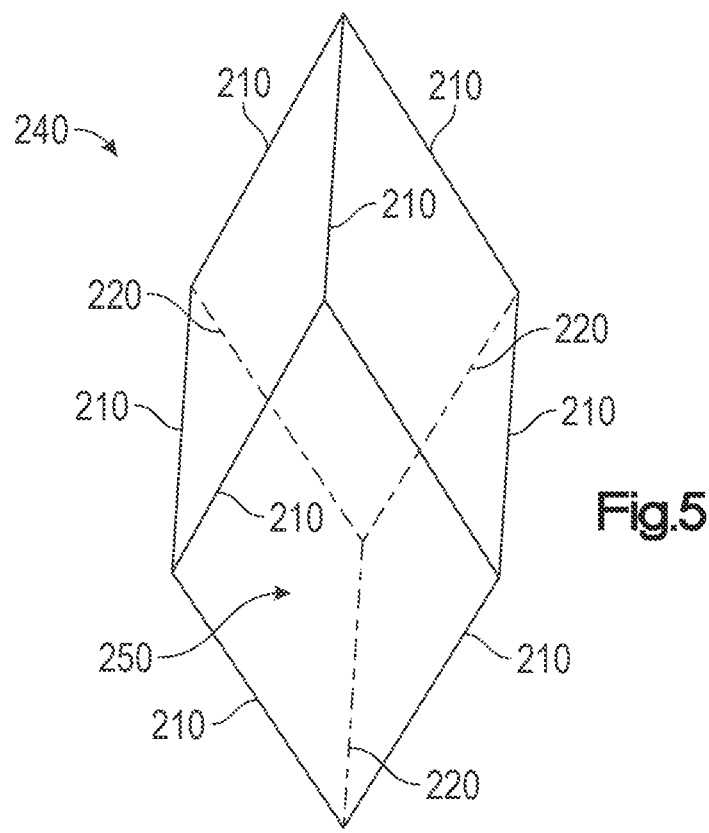
FIG. 5 is a simplified perspective view of another geometric structure of the unit cell of FIG. 3.

Each of the plurality of second geometric structures 240 has an internal volume 250 that is substantially equal to the internal volumes 250 of the other second geometric structures 240. As shown in FIG. 5, each second geometric structure 230 is formed by a number of internal struts 220 and a number of outer struts 210. Each second geometric structure 230 is illustratively a geometric trigonal trapezohedron. As illustrated in FIG. 3, the plurality of second geometric structures 240 within the first geometric structure 230 include four geometric trigonal trapezohedrons such that the unit cell structure 200 is a geometric rhombic trigonal trapezohedron (GRTT). As will be appreciated from the description below, a rhombic trigonal trapezohedron (RTT) can be configured as a geometric RTT (GRTT), and can alternatively be configured as an organic RTT (ORTT).

Figure 6:
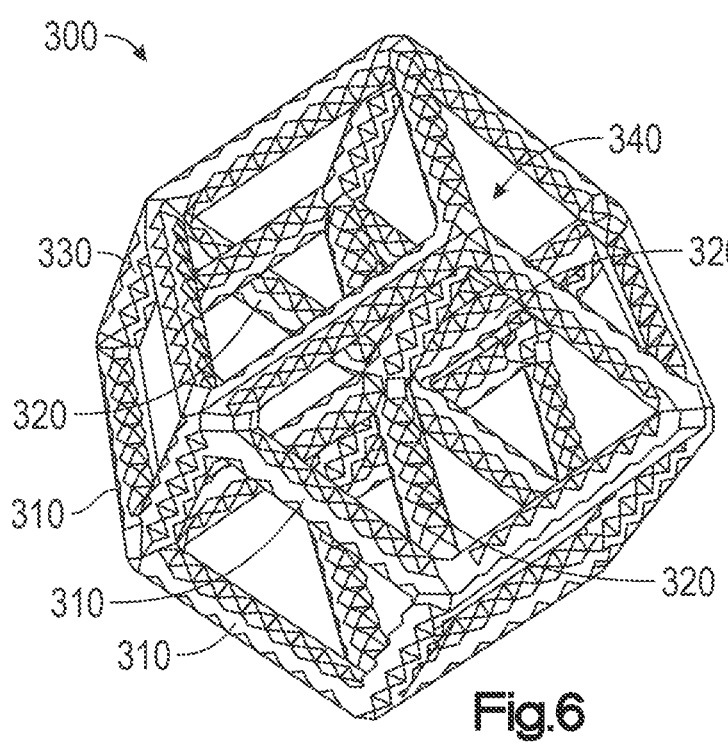
FIG. 6 is a perspective view of another embodiment of a unit cell of a porous structure for the orthopaedic prosthetic component of FIGS. 1-2.

It should be appreciated that each unit cell structure may include other types of second geometric structures. For example, as shown in FIG. 6, a unit cell structure 300 includes a plurality of outer struts 310 and a plurality of internal struts 320, which form a first geometric structure 330 and a plurality of second geometric structures 340 that are within the first geometric structure 330. In the illustrative embodiment, the first geometric structure 330, like the first geometric structure 230, comprises the plurality of outer struts 310 and is a geometric rhombic dodecahedron. The outer struts 310 can define constant thicknesses along entireties of their respective lengths. Further, the outer struts 310 can have equal thicknesses. The internal struts 320 can also define constant thicknesses along entireties of their respective lengths. Further, the internal struts 320 can have equal thicknesses. Further still, the internal struts 320 and the outer struts 310 can have equal thicknesses. Alternatively, the internal struts 320 and the outer struts 310 can have different thicknesses. In examples whereby the outer struts 310 and the internal struts 320 are cylindrical, the respective thicknesses define diameters of the outer struts 310 and the internal struts 320, respectively.

Figure 7:
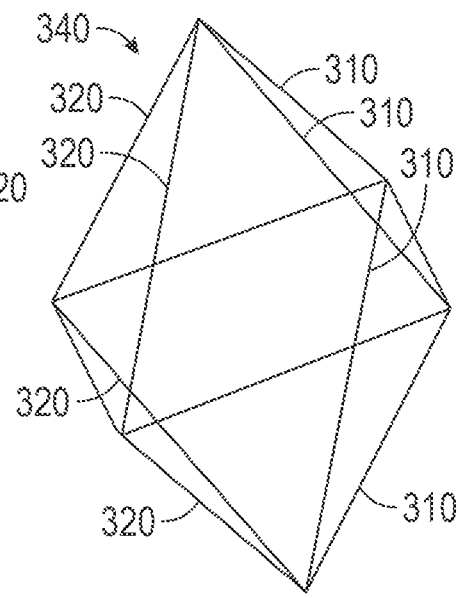
FIG. 7 is a simplified perspective view of another geometric structure of the unit cell of FIG. 3.

As shown in FIG. 7, each second geometric structure 340 is formed by a number of internal struts 320 and a number of outer struts 310. Each second geometric structure 340 is illustratively a geometric octahedron (e.g., a diamond-shaped structure). As illustrated in FIG. 6, the plurality of second geometric structures 340 within the first geometric structure 330 include six geometric octahedrons such that the unit cell structure 300 is a geometric rhombic octahedron (GRO).

Within the unit cell structures of the porous three-dimensional structure described above, at least one of a length and diameter of at least one strut within each unit cell can be configured to meet predetermined or desired geometric properties of the unit cell structure. In some examples, the at least one of a length and diameter of at least one strut within each unit cell of the organic structure can be modified with respect to a corresponding at least one strut of the geometric structure. These geometric properties can be selected from the group consisting of porosity, pore size, minimum window size, and combinations thereof. It was advantageously discovered that certain geometric structures (discussed below) of the unit cell structure could optimize one or more of these geometric properties to provide a more robust, and homogenous, geometry. The resulting geometry provides for enhanced bone ingrowth while maintaining the requisite porous structure stability.

Figure 8:
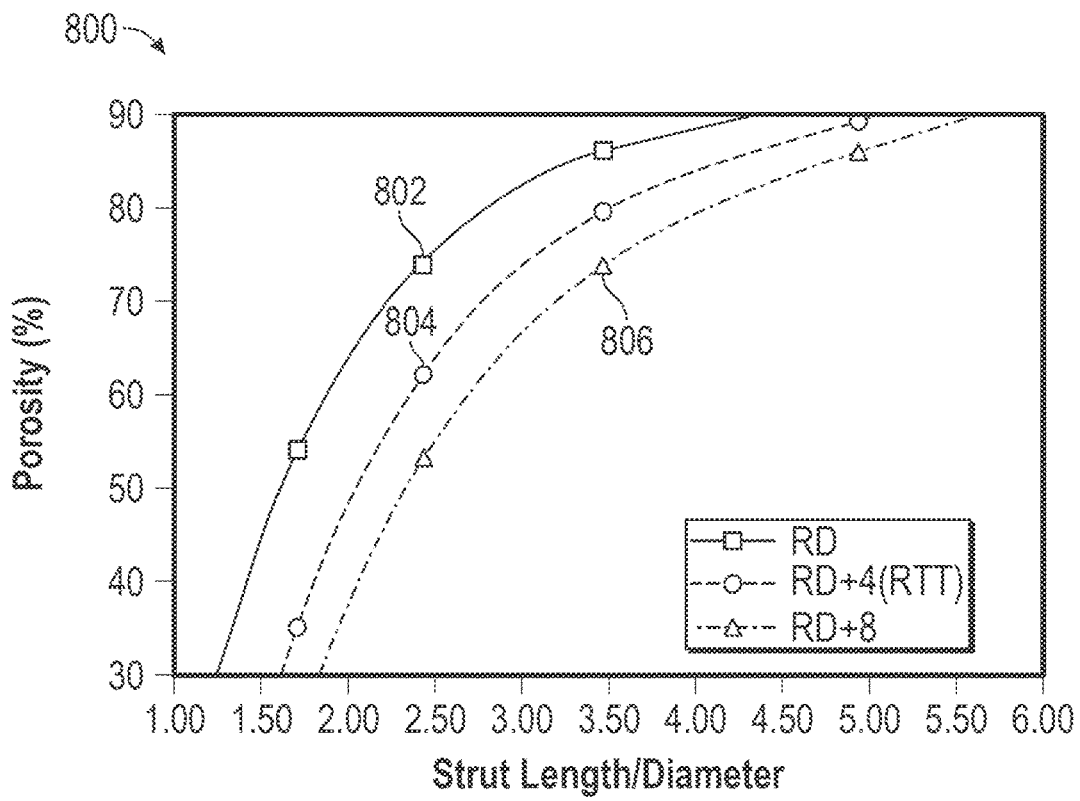
FIG. 8 illustrates a chart of porosity percentage versus strut length/diameter for various unit cell geometries, in accordance with various embodiments.

Turning to porosity, the porous structure 120 has a porosity of between about 50% and about 75%. As discussed above, the term "about" refers to a range associated with typical manufacturing tolerances. In that way, a porosity of "about 50%" may be porosity of 50% plus or minus a typical manufacturing tolerance such as, for example, 2% (i.e., a range of 48% to 52%). In other embodiments, the porosity of the porous three-dimensional structure is between about 20% and about 95%. In other embodiments, the porosity is in a range of between about 35% and about 85%. Geometrically, the porosity of the unit cell structure is dependent on the ratio of the strut length (a) to the strut diameter (d). FIG. 8, for example, a chart 800 of porosity percentage versus strut length/diameter for various unit cell geometries is provided, in accordance with various embodiments. As outlined in the chart 800, three particular unit cell geometries/structures were examined, namely a geometric rhombic dodecahedron (GRD) (see, e.g., FIG. 4), a geometric rhombic dodecahedron provided with four internal struts (GRD+4) (or geometric rhombic trigonal trapezohedron) (see, e.g., FIG. 3), and a geometric rhombic dodecahedron provided with eight internal struts (GRD+8) (or geometric rhombic octahedron) (see, e.g., FIG. 6). For each of the structures, porosities were obtained at several a/d ratios from a design file for each unit cell structure and the relationship for each unit cell structure modeled by fitting the data to a fourth order polynomial equation of the form:

$$\text{Porosity} = A*(a/d)^4 + B*(a/d)^3 + C*(a/d)^2 + D*(a/d) + E \tag{1}$$

Wherein A, B, C, D, and E are constants. In this comparison, the structure dimensions were derived geometrically from the strut length and diameter of each unit cell structure.

As observed in the chart 800 of FIG. 8, the geometric RD structure generally possesses a greater porosity at a given a/d ratio, which is to be expected given its lack of internal struts compared to the geometric RD+4 and geometric RD+8 structures. The porosity for the geometric RD structure is illustrated by the line 802. However, this decrease in porosity in the geometric RD+4 and geometric RD+8 structures, illustrated by lines 804, 806, respectively, enables designs made with them to reach combinations of relatively lower porosity, lower pore size, and relatively higher window size at a constant strut diameter (fixed by the build resolution of the printer) not possible with the geometric RD, as described in greater detail below.

Figure 9:
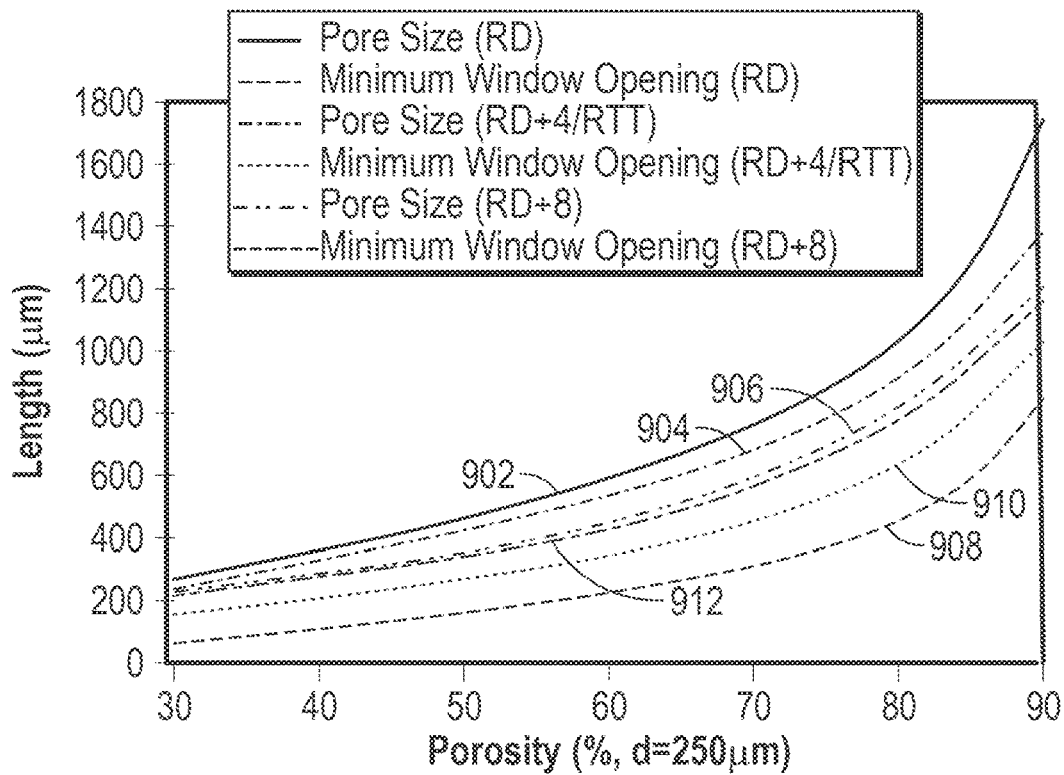
FIG. 9 illustrates a chart of pore size and minimum pore window opening size versus porosity percentage for various unit cell geometries, in accordance with various embodiments.

Referring now to FIG. 9, a chart 900 of pore size and minimum window size versus porosity percentage for various unit cell geometries/structures is provided, in accordance with various embodiments. As in FIG. 8, three particular unit cell structures were examined, namely a rhombic dodecahedron (GRD) (see, e.g., FIG. 4), a geometric rhombic dodecahedron provided with four internal struts (GRD+4) (or geometric rhombic trigonal trapezohedron) (see, e.g., FIG. 3), and a geometric rhombic dodecahedron provided with eight internal struts (GRD+8) (or geometric rhombic octahedron) (see, e.g., FIG. 6). The pore size of the geometric rhombic dodecahedron, for example, was taken as the equivalent diameter of a sphere within the volume bounded within the geometric rhombic dodecahedron unit cell, and the volume was calculated by taking the volume of the geometric rhombic dodecahedron of strut length (a) and subtracting the volume of each strut within or bounded by the geometric rhombic dodecahedron. The equations provided herein for calculating pore size (PS) depend on the strut length (a), diameter (d), and porosity in decimal units (p). The equations are as follows:

For the SRD structure:

$$PS = a * \sqrt[3]{6/\pi} * \sqrt[3]{\frac{16*\sqrt{3}*p}{9} - \frac{4d}{a}*\left(1 - \frac{\sqrt{2}d}{2a}\right)^2} \tag{2}$$

For the SRD+4 structure:

$$PS = \sqrt[3]{\frac{6}{4\pi}*\left[(1-\{1-p\})*\left(\frac{16}{9}*\sqrt[2]{3}*a^3\right) - 0.5*(\pi*d^2*\{\sqrt[2]{3}*a - 0.75*d\} - d^3*\{4 - 2\sqrt[2]{2}\})\right]} \tag{3}$$

For the SRD+8 structure:

$$PS = \sqrt[3]{\frac{6}{8\pi}*\left[(1-\{1-p\})*\left(\frac{16}{9}*\sqrt[2]{3}*a^3\right) - \pi*d^2*\{2a-d\} + 4.5d^3*\{2\sqrt[2]{2} - \sqrt[2]{6}\}\right]} \tag{4}$$

The line 902 in the chart 900 illustrates the relationship between pore size and porosity percentage for the geometric rhombic dodecahedron (SRD). The line 904 illustrates the relationship between pore size and porosity percentage for the geometric rhombic trigonal trapezohedron (SRD+4), and the line 906 illustrates the relationship between pore size and porosity percentage for the geometric rhombic octahedron (SRD+8).

As observed in the chart 900 of FIG. 9, at lower porosity percentages, the three structures generally provided similar required pore sizes. However, as the given porosity percentage increases (and assuming that the strut diameters remain substantially the same), the required pore size in the SRD structure to accommodate the porosity percentage becomes significantly greater than the other structures, thus putting more stringent requirements on the SRD structure as required porosity increases by causing the pore size to increase to beyond what may be effective for bone in-growth. In other words, as required porosity percentage increases, the less effective the SRD structure becomes, which is noteworthy when designing porous three-dimensional structures such as those discussed herein.

Figure 10:
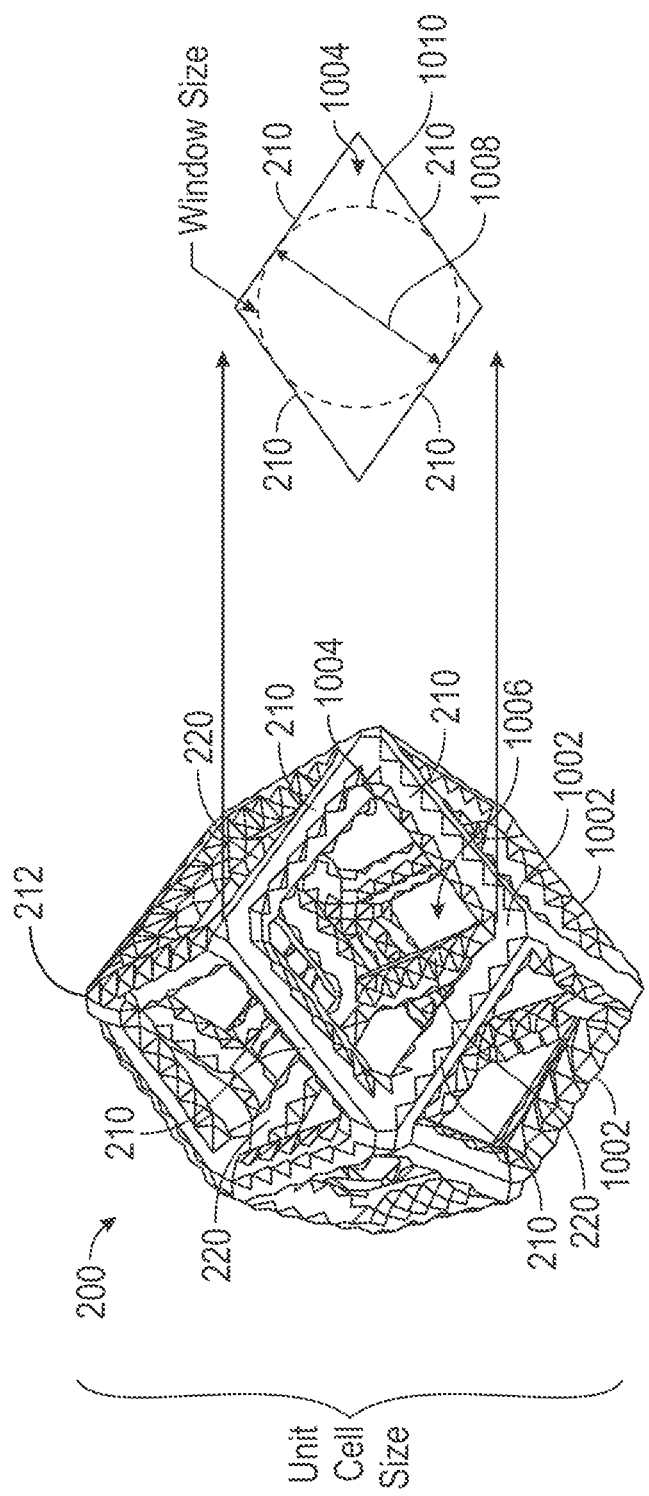
FIG. 10 illustrates an association of window size to a unit cell structure, in accordance with various embodiments.
Figure 11:
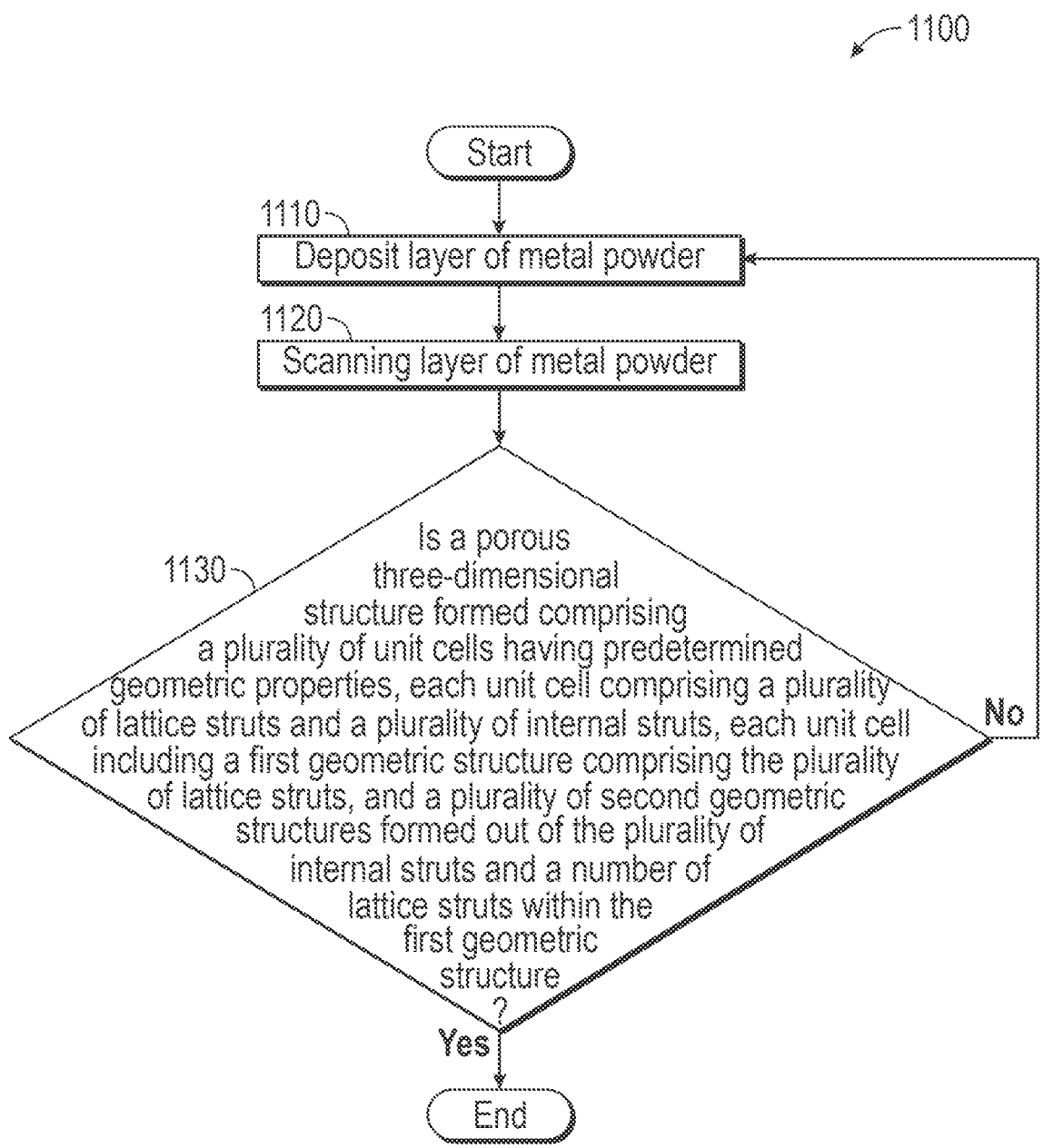
FIG. 11 illustrates a workflow for producing a porous three-dimensional structure, in accordance with various embodiments.

Referring now to FIG. 10, each unit cell structure 200 has a plurality of outer faces 1002 and the outer struts 210 cooperate to define a number of openings 1004 in the outer faces 1002. The internal struts 220 of the unit cell structure 200 cooperate with a number of outer struts 210 to form a number of internal openings 1006. The minimum window opening or size of each of the openings 1004, 1006 may be defined as the diameter 1008 of a circle 1010 positioned in the corresponding opening (illustratively one of the openings 1004 in FIG. 10) such that each strut 210 (or strut 220) is positioned on a tangent line of the circle 1010. The lengths and diameters of the struts thereby determine the size of each of the openings 1004, 1006 and, by extension, the diameter of the largest sphere that can fit therein. For example, for a given strut length, as the strut diameter increases, the minimum window opening would decrease.

These associations are provided by the following equation, which was used to calculate minimum window opening for all structures (e.g., SRD, SRD+4, SRD+8, etc.) and generate the lines 908, 910, 912 in FIG. 9:

$$m = \tfrac{2}{3}\sqrt{2} \cdot a - d \tag{5}$$

For the purposes of the chart 900, the minimum window opening is the diameter of the largest circle 1010 that can fit in each opening. In other words, it is the diameter of the inscribed circle and, as such, is dependent on the strut length (a) and diameter (d). The relationship between window size versus porosity percentage for various unit cell geometries. The line 908 in the chart 900 illustrates the relationship between minimum window opening versus porosity for the geometric rhombic dodecahedron (GRD). The line 910 illustrates the relationship between minimum window opening versus porosity for the geometric rhombic trigonal trapezohedron (GRD+4), and the line 912 illustrates the relationship between minimum window opening versus porosity for the geometric rhombic octahedron (GRD+8).

As observed on the chart 900 in FIG. 9, at generally all porosity percentages, there exists a generally uniform gap in the minimum window opening for between each unit cell structure. As such, regardless of required porosity percentage for a given porous three-dimensional structure with a substantially constant strut diameter, the SRD+8 structure will possess a greater minimum window opening than the SRD+4 and SRD structures, and both the SRD+8 and SRD+4 structures will possess a greater minimum window opening than the SRD structure, to a given porosity percentage.

The results in FIG. 9 establish that the structures having internal struts, namely SRD+4, and to a lesser extent SRD+8, are advantageous over the SRD structure. The SRD+4 and SRD+8 enable smaller pore size at a given porosity and strut diameter. Whatever advantage the SRD structure would seem to have in porosity as a function of a/d ratio almost entirely diminishes as the required a/d ratio increases. Finally, the SRD+4 and SRD+8 structures (or structures with internal struts) provide the most homogenous structure by providing a smaller difference between pore size and window size than the SRD structure.

In the porous structure 120, the ratio of the pore size of a unit cell to any of its corresponding window sizes is in a range of 1.50 to 1.60. In other embodiments, the ratio may be in a range of 1.00 to 1.10. In still other embodiments, the ratio may be 1.00 to 2.90. As shown in FIG. 9, the difference between pore size and window size is substantially less for the SRTT structure of FIG. 3 and the SRO structure of FIG. 6 than the SRD structure of FIG. 4. As a consequence, the SRTT structure advantageously provides for a more homogeneous structure, with a smaller difference between the pore window size and overall pore size, especially at high levels of porosity, which promotes bone in-growth by providing window sizes closely in proportion of the pore size. Though only SRTT is referenced in FIG. 9, the conclusion would hold for various structures that include internal struts, for example, structures with internal struts in multiples of four.

In accordance with various embodiments, an orthopaedic implant is provided. The implant can include a porous three-dimensional structure comprising a lattice of connected unit cells, as illustrated, for example, by the unit cell structure of FIGS. 3-5. The at least one unit cell can comprise a plurality of outer struts. The at least one unit cell can further comprise a first geometric structure comprising the plurality of outer struts, and a second geometric structure sharing a subset of the plurality of outer struts of the first geometric structure and having a different geometry from the first geometric structure (see FIGS. 3 and 6). Further, at least a portion of the subset of the plurality of outer struts in the second geometric structure can intersect to form angles substantially equal to the angles formed by intersections of the plurality of outer struts of the first geometric structure.

As discussed above, the first geometric structure can be a geometric rhombic dodecahedron as illustrated, for example, in FIG. 4. The second geometric structure can be a geometric trigonal trapezohedron (see FIG. 5). The geometric trigonal trapezohedron can be formed by inserting four struts into the first geometric structure as illustrated, for example, in FIG. 3. Further, the at least one unit cell can include four geometric trigonal trapezohedron structures within the first geometric structure as illustrated, for example, in FIG. 3.

Within the porous three-dimensional structure, at least one of a length and diameter of at least one strut within the lattice can be configured to meet predetermined geometric properties of the lattice. In one example, the at least one of a length and diameter of at least one strut of the organic structure can be modified with respect to the at least one of a length and diameter of at least one strut of the geometric structure. As discussed above, these geometric properties can be selected from the group consisting of, porosity, pore size, minimum opening size, and combinations thereof. For example, the porosity can be between about 20% and about 95%. The porosity can also be between about 35% and about 85%. The porosity can also be between about 50% and about 75%. Further, the individual strut lengths can be, for example, about 25% to about 175% of the average strut length of the plurality of struts. As will be described in more detail below each of the geometric structures described above can be modified so as to produce an organic structure. In one example, the individual outer strut lengths of the each of the geometric structures can also be modified to be, for example, up to about 75% to about 125% of the average strut length of the plurality of outer struts of the geometric structures so as to produce the organic structure. In another example, the individual outer strut lengths of the each of the geometric structures can also be modified to be, for example, up to about 50% to about 150% of the average strut length of the plurality of outer struts of the geometric structures.

In accordance with various embodiments, an orthopaedic implant is provided. The implant can include a porous three-dimensional structure comprising a plurality of repeating unit cells. Each unit cell can include a base geometric structure, and a secondary geometric structure formed out of a portion of the base geometric structure and having a different geometry from the base geometric structure. Further, for a given porous three-dimensional structure porosity, at least one unit cell can have a pore size that is different from the average geometric structure pore size of the porous three-dimensional structure and a window size that is different from the average geometric structure window size of the porous three-dimensional structure.

Figure 12C:
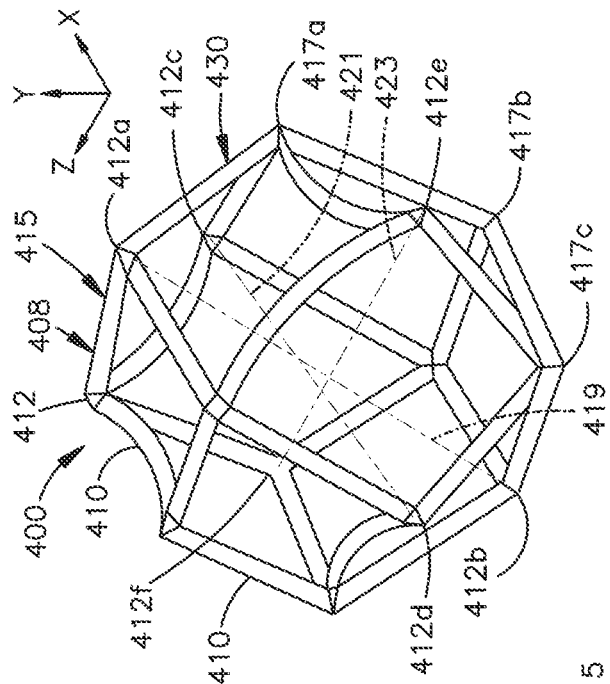
FIG. 12C is a perspective view of an organic structure that is 50% modified with respect to the geometric structure illustrated in FIG. 12A.
Figure 12B:
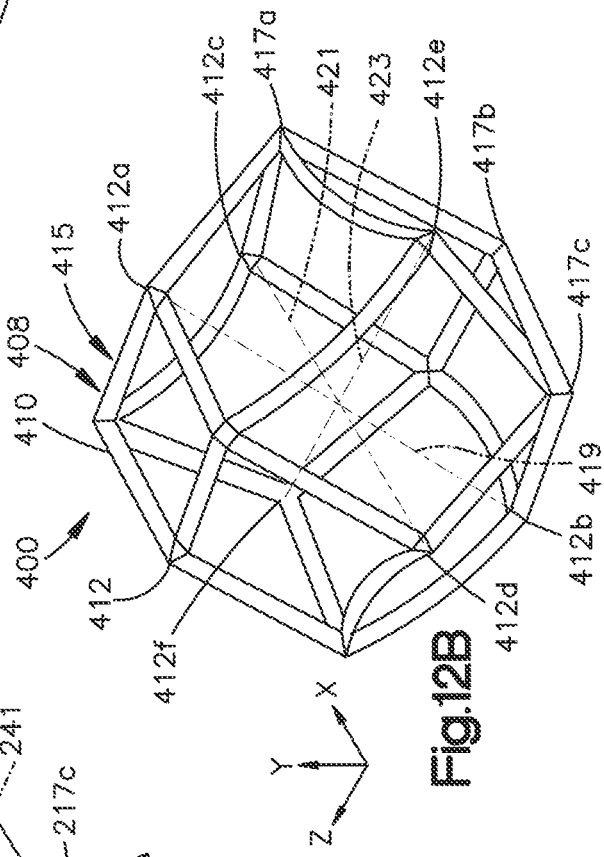
FIG. 12B is a perspective view of an organic structure that is 25% modified with respect to the geometric structure illustrated in FIG. 12A.
Figure 12A:
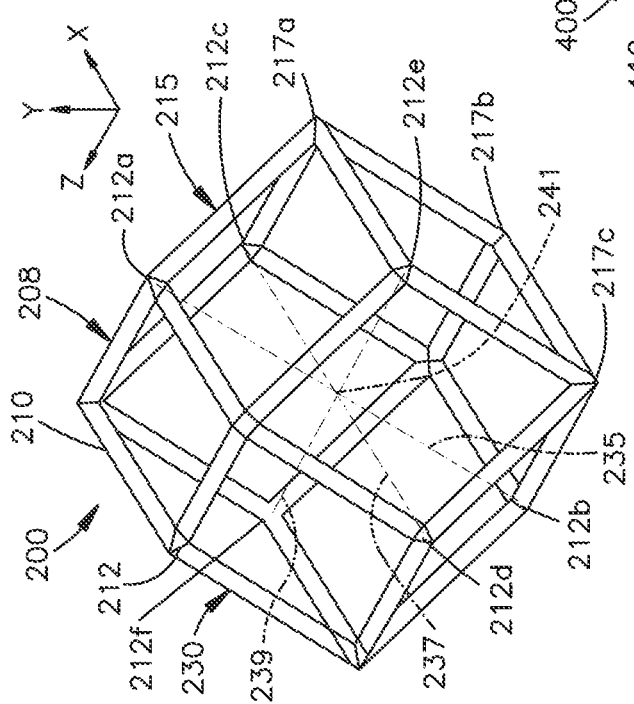
FIG. 12A is another perspective view of the geometric structure of the unit cell of FIG. 4.

Referring now to FIGS. 12A-13E generally, organic unit cell structures 400 can be modified with respect to the geometric unit cell structures 200 described above. For instance, FIGS. 12A and 13A show the first or outer geometric structure 230. FIGS. 12B-12C and FIGS. 13B-13E show a first or organic outer structure having node positions that differ from those of the corresponding first geometric structure 230. In one example illustrated in FIGS. 12A, the first geometric structure 230 is illustrated as the geometric rhombic dodecahedron 215 as described above. As illustrated in FIGS. 12B-C, an organic structure 430 can be configured as an organic rhombic dodecahedron 415 that is modified with respect to the geometric rhombic dodecahedron described above. For instance, one or more of the nodes up to all of the nodes of the organic structure 430 are repositioned with respect to the corresponding nodes of the geometric structure 230.

As shown in FIG. 12A, each of the plurality of outer nodes 212 has a position in three-dimensional space (e.g., along an x-direction, a y-direction, and a z-direction that are all oriented perpendicular to each other) with respect to the remaining outer nodes 212 of the plurality of outer nodes 212 that define the outer nodes 212 of the geometric rhombic dodecahedron 215.

Further, the outer nodes 212 include respective pairs of opposed nodes. As one example, first and second outer nodes 212a and 212b of the outer nodes 212 define a first pair of opposed outer nodes. The nodes of a pair of opposed outer nodes can be spaced further from each other than from any other node. In this regard, none of the outer nodes 212 is spaced further from the first outer node 212a than the second outer node 212b. Further, none of the outer nodes 212 is spaced further from the second outer node 212b than the first outer node 212a. Additionally, the nodes of a pair of opposed outer nodes can be spaced from each other by three intermediate outer nodes of the plurality of outer nodes 212 along a shortest path along the outer struts 210 from and to the nodes of the pair of opposed outer nodes. Thus, the second outer node 212b is spaced from the first outer node 212a by three intermediate outer nodes of the plurality of outer nodes 212 along a shortest path along the outer struts 210 from the first outer node 212a to the second outer node 212b. That is, when traveling along the outer struts 210 from the first outer node 212a to the second outer node 212b along the shortest path, the path includes three intermediate outer nodes 217a, 217b, and 217c (it being recognized that multiple such shortest paths are defined).

Third and fourth outer nodes 212c and 212d of the outer nodes 212 define a second pair of opposed nodes. Fifth and sixth outer nodes 212e and 212f of the outer nodes 212 define a third pair of opposed nodes. It is recognized that a first straight imaginary line 235 extends through the first outer node 212a and the second outer node 212b. A second straight imaginary line 237 extends through the third outer node 212c and the fourth outer node 212d. A third straight imaginary line 239 extends through the fifth outer node 212e and the sixth outer node 212f. The first straight imaginary line 235, the second straight imaginary line 237, and the third straight imaginary line 239 substantially intersect each other at a point of intersection 241.

Referring now to FIGS. 1 and 12B, at least some up to all of the unit cells of the porous structure 120 of the implant 100 have an organic unit cell structure 400 shown in FIG. 12B. In some examples, the organic unit cell structure 400 is modified with respect to the geometric rhombic dodecahedron 215 illustrated in FIG. 4. In other examples, the organic unit cell structure 400 is designed without the aid of a previously-designed geometric unit cell structure 200, such as the geometric rhombic dodecahedron described above. Therefore, as shown in FIG. 12B, each organic unit structure includes a plurality of struts 408 that include a plurality of outer struts 410. The outer struts 410 combine to define a lattice structure. The outer struts 410 cooperate to form an organic outer structure 430 that is modified with respect to the geometric outer structure 230 of FIG. 4. In the illustrative embodiment, the organic outer structure 430 is an organic rhombic dodecahedron 415. The outer struts 410 can define constant thicknesses along entireties of their respective lengths. Further, the outer struts 410 can have equal thicknesses. The internal struts 420 can also define constant thicknesses along entireties of their respective lengths. Further, the internal struts 420 can have equal thicknesses. Further still, the internal struts 420 and the outer struts 410 can have equal thicknesses. Alternatively, the internal struts 420 and the outer struts 410 can have different thicknesses. In examples whereby the outer struts 410 and the internal struts 420 are cylindrical, the respective thicknesses define diameters of the outer struts 410 and the internal struts 420, respectively.

The outer struts 410 thus intersect each other so as to define a plurality of outer vertices or outer nodes 412. Each of the outer nodes 412 is defined by an intersection of three of the outer struts 410. Each of the outer struts 410 therefore extends from a respective first node of the outer nodes 412 to a respective second node of the outer nodes 412 along a respective length. When the outer struts 410 define the organic rhombic dodecahedron 415, the struts 410 combine to define fourteen outer nodes 412. Further, each of the plurality of outer nodes 412 has a position in three-dimensional space (e.g., along an x-direction, a y-direction, and a z-direction that are all oriented perpendicular to each other) with respect to the remaining outer nodes 412 of the plurality of outer nodes 412 that define the nodes 412 of the organic rhombic dodecahedron 415.

As discussed above, the position of at least one the outer nodes 412 of the organic rhombic dodecahedron 415, including a plurality of the outer nodes 412 up to all of the outer nodes is different than the respective at least one outer node 212 of the geometric rhombic dodecahedron. Referring to FIG. 12B, the outer struts 410 and outer nodes 412 combine to substantially define the geometric structure 430 that is within 25% of the geometric rhombic dodecahedron 215. For instance, the position of at least one outer node 412 of the organic rhombic dodecahedron 415 is up to 25% modified with respect to the position of the corresponding at least one outer node 212 of the geometric rhombic dodecahedron 215 shown in FIG. 12A. For instance, the position of a plurality of outer nodes 412 of the organic rhombic dodecahedron 415 is up to 25% modified with respect to the position of the corresponding plurality of outer nodes 212 of the geometric rhombic dodecahedron 215. Thus, the outer struts 410 and outer nodes 412 combine to substantially define a geometric structure that is within 25% of the geometric rhombic dodecahedron 215. Further, the position of at least one of the outer nodes 412 up to a plurality of the outer nodes 412 of the organic rhombic dodecahedron 415 illustrated in FIG. 12B can be the same as the position of a corresponding at least one of the outer nodes 212 up to a corresponding plurality of the outer nodes 212 of the geometric rhombic dodecahedron 215 shown in FIG. 12A. The term "within" as used herein with reference to a percentage includes the stated percentage.

The position of the outer nodes 412 of the organic rhombic dodecahedron 415 can be expressed by the following equation:

$$\text{Modified Position} N_i^{p\%} = N_i + p\% f(x_i, y_i, z_i) \tag{6}$$

Wherein N identifies a node, "i" identifies the particular node of the geometry, p is the change in position expressed as a percentage of the position of the node of the geometric structure, and x, y, and z are positional coordinates of the node "i" of the geometric structure. The modified position of the node of the organic structure 430 can differ from the position of the corresponding node of the geometric structure 230 along any one or more up to all of the x-direction, the y-direction, and the z-direction.

In another embodiment, referring to FIG. 12C, the outer struts 410 and outer nodes 412 combine to substantially define the geometric structure 430 that is within 50% of the geometric rhombic dodecahedron 215. For instance, the position of at least one outer node 412 of the organic rhombic dodecahedron 415 is up to 50% modified with respect to the position of the corresponding at least one outer node 212 of the geometric rhombic dodecahedron 215 shown in FIG. 12A. For instance, the position of a plurality of outer nodes 412 of the organic rhombic dodecahedron 415 is up to 50% modified with respect to the position of the corresponding plurality of outer nodes 212 of the geometric rhombic dodecahedron 215. Thus, the outer struts 410 and outer nodes 412 combine to substantially define a geometric structure that is within and including 50% of the geometric rhombic dodecahedron 215. Further, the position of at least one of the outer nodes 412 up to a plurality of the outer nodes 412 of the organic rhombic dodecahedron 415 illustrated in FIG. 12C can be the same as the position of a corresponding at least one of the outer nodes 212 up to a corresponding plurality of the outer nodes 212 of the geometric rhombic dodecahedron 215 shown in FIG. 12A.

Thus, as illustrated in FIGS. 12A-12C, at least some of the outer nodes 412 of the organic rhombic dodecahedron are repositioned with respect to the outer nodes 212 of the geometric rhombic dodecahedron 215. Accordingly, when a first porous three-dimensional structure including the organic outer structure 430 is superimposed onto a second porous three-dimensional structure including the geometric structure 230 at the same position and orientation, at least some of the outer nodes 412 of the first porous three-dimensional structure are offset with respect to a corresponding some of the nodes 212 of the second porous three-dimensional structure. In some examples, other outer nodes 412 of the plurality of outer nodes 412 of the first porous three-dimensional structure are coincident with corresponding other outer nodes 212 of the plurality of nodes 212 of the second porous three-dimensional structure. The organic outer structure 430 is otherwise substantially identical to the geometric outer structure 230 but for the repositioned outer nodes 412 and resulting changes to the respective struts 410 as will now be described. For instance, the organic outer geometry 430 and resulting porous three-dimensional structure has an equal number of struts and nodes, respectively, as the geometric outer structure 230 and the resulting porous three-dimensional structure.

It has been found that the porous three-dimensional structure having the organic structure 430 has a ductility that is greater than the ductility of the porous three-dimensional structure that includes the geometric outer structure 230. Further, the porous three-dimensional structure including the organic outer structure 430 has suitable structural integrity when implanted in a human anatomy.

In particular, as a result of the repositioned outer nodes 412, at least one or more up to all of the struts 410 of the organic outer structure 430 have at least one geometric property that is different than the corresponding struts 210 of the geometric outer structure 230. As described above, the geometric property can include at least one of a length, orientation, and path type (e.g., straight or bent) of the strut 210. For instance, at least one or more of the outer struts 410 that partially define a repositioned outer node 412 can be longer or shorter than the corresponding outer struts 210 of the corresponding geometric rhombic dodecahedron. In this regard, the outer struts 410 extend from and to a respective pair of the outer nodes 412 along respective lengths, and the lengths of at least some of the outer struts 410 are different than each other. For instance, the individual lengths of the outer struts 410 can also be modified to be, for example, about 75% to about 125% of the average strut length of the plurality of outer struts 410.

Further, the outer struts 410 can extend along any suitable path along its length from and to the adjacent nodes 412 that are defined by the outer struts 410. For instance, or more of the struts 410 that partially define a repositioned outer node 412 can extend along a straight and linear path along an entirety of its respective length, and can have a different orientation than the outer struts 210 of the corresponding geometric structure 230. Alternatively, at least a portion of at least one or more of the outer struts 410 that partially define a repositioned outer node 412 can be bent along its length between a respective first outer node 412 of the plurality of nodes to a respective second outer node 412 of the plurality of nodes. Thus, the at least one bent strut 410 intersects two different other pairs of struts 410 so as to define the respective first and second outer nodes 412. In one example, the at least a portion of the outer strut 410 extends along a curved path. Alternatively or additionally, at least a portion of at least one or more of the outer struts 410 can be angulated and thus bent. It is appreciated that all of the outer struts 410 illustrated in FIGS. 12B-12C can be straight (see FIGS. 13C and 13E). Alternatively, all of the outer struts 410 can be bent.

With continuing reference to FIG. 12B, the outer struts 410 include a longest outer strut and a shortest outer strut. None of the outer struts 410 extend between respective adjacent outer nodes 412 along a path that is longer than that of the longest outer strut. Conversely, none of the outer struts 410 extend between respective adjacent outer nodes 412 along a path that is shorter than that of the longest outer strut. When the positions of the outer nodes 412 of the organic structure 430 are 25% modified with respect to the position of the corresponding geometric outer structure 230, the length of the shortest outer strut 410 is no less than approximately 60% of that of the longest outer strut 410.

As illustrated in FIG. 12C, the outer struts 410 include a longest outer strut and a shortest outer strut. None of the outer struts 410 extend between respective adjacent outer nodes 412 along a path that is longer than that of the longest outer strut. Conversely, none of the outer struts 410 extend between respective adjacent outer nodes 412 along a path that is shorter than that of the longest outer strut. When the positions of the outer nodes 412 are 50% modified with respect to the position of the outer nodes 212 of the corresponding geometric outer structure 230, the length of the shortest outer strut 410 is no less than approximately ⅓ of that of the longest outer strut 410.

With continuing reference to FIGS. 12B-12C, the outer nodes 412 include a first outer node 412a and a second outer node 412b opposite the first outer node 412a so as to define a first pair of opposed nodes. The outer nodes 412 further include a third outer node 412c and a fourth outer node 412d opposite the third outer node 412c so as to define a second pair of opposed nodes. The outer nodes 412 further include a fifth outer node 412e and a sixth outer node 412f opposite the fifth outer node 412e so as to define a third pair of opposed nodes.

As described above with respect to FIG. 12A, nodes of a pair of opposed outer nodes 412 can be spaced further from each other than from any other node. In this regard, none of the outer nodes 412 is spaced further from the first outer node 412a than the second outer node 412b. Further, none of the outer nodes 412 is spaced further from the second outer node 412b than the first outer node 412a. Additionally, the nodes of a pair of opposed outer nodes can be spaced from each other by three intermediate outer nodes of the plurality of outer nodes 412 along a shortest path along the outer struts 410 from and to the nodes of the pair of opposed outer nodes. Thus, the second outer node 412b is spaced from the first outer node 412a by three intermediate outer nodes of the plurality of outer nodes 412 along a shortest path along the outer struts 410 from the first outer node 412a to the second outer node 412b. That is, when traveling along the outer struts 410 from the first outer node 412a to the second outer node 412b along the shortest path, the path includes three intermediate outer nodes 417a, 417b, and 417c (it being recognized that multiple such shortest paths are defined).

A first straight imaginary line 419 extends geometric the first outer node 412a and the second outer node 412b. A second straight imaginary line 421 extends through the third outer node 412c and the fourth outer node 412d. A third straight imaginary line 423 that extends through the fifth outer node 412e and the sixth outer node 412f. The first and second straight imaginary lines 419 and 421 intersect each other at a first intersection 424a with respect to a select view of the porous three-dimensional structure. The third straight 423 line intersects the first straight imaginary line 419 at a second intersection that is offset from the first intersection with respect to the select view of the porous three-dimensional structure. The third straight imaginary line 423 can also intersect the second straight imaginary line 421 at a third intersection that is offset from either or both of the first and second intersections with respect to the select view of the porous three-dimensional structure.

The organic unit cell structure 400 of FIGS. 12B-12C can be modified with respect to the geometric unit cell structure 200, such that the outer nodes 412 of the organic unit cell structure 400 are repositioned with respect to the corresponding outer nodes 212 of the geometric unit cell structure 200 in any suitable direction. Thus, outer nodes 412 of a first half of the organic unit cell structure 400 can be repositioned with respect to the corresponding outer nodes 212 of the geometric unit cell structure 200 in a first direction. The outer nodes 412 of a second half of the organic unit cell structure 400 can be repositioned with respect to the corresponding outer nodes 212 of the geometric unit cell structure 200 in a second direction different than the first direction. The first and second directions can be opposite each other, perpendicular to each other, or oblique to each other. The first and second halves of the organic unit cell structure 400 are separated from each other by a plane that bisects the organic unit cell structure 400. Thus, in some examples, no matter the orientation of the plane (i.e., for all orientations of the plane), it is the case that at least some up to all of the outer nodes 412 of the first half of the organic unit cell structure 400 are repositioned with respect to the corresponding outer nodes 212 of the geometric unit cell structure 200 in different directions, and at least some up to all of the outer nodes 412 of the second half of the organic unit cell structure 400 are repositioned with respect to the corresponding outer nodes 212 of the geometric unit cell structure 200 in different directions.

Figure 13A:
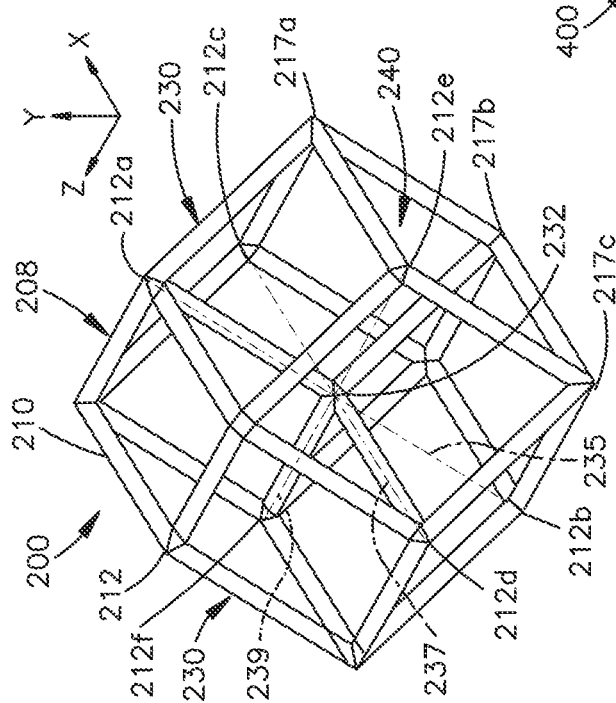
FIG. 13A is another perspective view of the geometric structure of the unit cell of FIG. 3.

Referring now to FIG. 13A, and as described above with respect to FIG. 3, the struts 208 include a plurality of outer struts 210 that define the first geometric structure 230. The struts 208 further include a plurality of internal struts 220 that, in combination with the outer struts 210, form the plurality of second geometric structures 240 that are within the first geometric structure 230. In the illustrative embodiment, the first geometric structure 230 comprises the plurality of outer struts 210. As described above, the plurality of outer struts 210 of FIG. 3 cooperate to form a geometric rhombic dodecahedron. Thus, the first geometric structure 230 defines a geometric rhombic dodecahedron. The internal struts 220 intersect each other so as to define an internal node 232. In particular, all of the internal struts 220 intersect each other to define the internal node 232. Further, each of the internal struts 220 extends from a respective outer node 212 to the internal node 232. In the illustrated embodiment, the internal struts 220 intersect each other so as to define only the single internal node 232 and no other internal nodes. Thus, the geometric unit cell 200 defines only one single internal node 232 that is internal with respect to the outer nodes 212.

The outer struts 210 can define constant thicknesses along entireties of their respective lengths. Further, the outer struts 210 can have equal thicknesses. The internal struts 220 can also define constant thicknesses along entireties of their respective lengths. Further, the internal struts 220 can have equal thicknesses. Further still, the internal struts 220 and the outer struts 210 can have equal thicknesses. Alternatively, the internal struts 220 and the outer struts 210 can have different thicknesses. In examples whereby the outer struts 210 and the internal struts 220 are cylindrical, the respective thicknesses define diameters of the outer struts 210 and the internal struts 220, respectively.

As illustrated in FIG. 13A, each of the plurality of second geometric structures 240 has an internal volume that is substantially equal to the internal volumes of the other second geometric structures 240. Each second geometric structure 230 is formed by a number of internal struts 220 and a number of outer struts 210. Each second geometric structure 230 is illustratively a geometric trigonal trapezohedron. As illustrated in FIG. 3, the plurality of second geometric structures 240 within the first geometric structure 230 include four geometric trigonal trapezohedrons such that the unit cell structure 200 is the geometric rhombic trigonal trapezohedron (GRTT).

The first geometric structure 230 includes the first, second, and third pairs of outer nodes 212 as described above with respect to FIG. 12A. Thus, the first straight imaginary line 235 extends through the first outer node 212a and the second outer node 212b. The second straight imaginary line 237 extends through the third outer node 212c and the fourth outer node 212d. The third straight imaginary line 239 extends through the fifth outer node 212e and the sixth outer node 212f. The first straight imaginary line 235, the second straight imaginary line 237, and the third straight imaginary line 239 substantially intersect each other at the internal node 232.

Figure 13C:
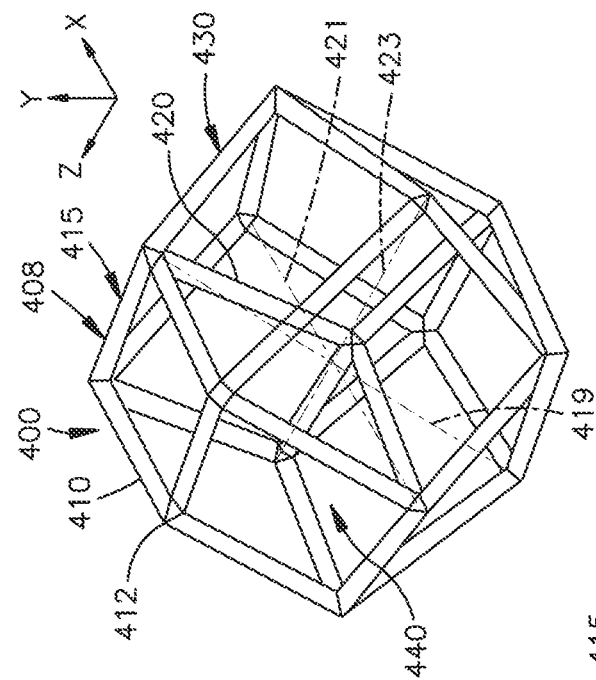
FIG. 13C is perspective view of the organic structure of FIG. 13B, showing all straight outer struts.
Figure 13B:
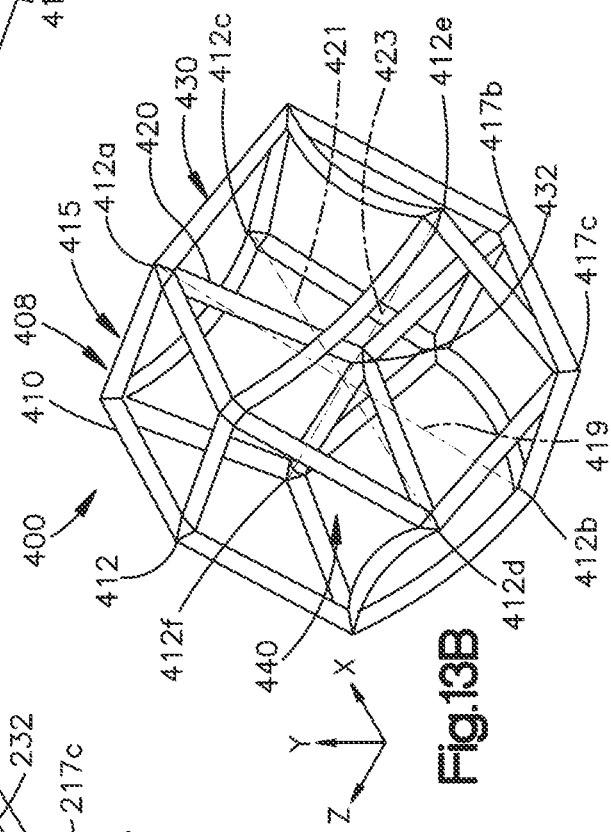
FIG. 13B is perspective view of an organic structure that is 25% modified with respect to the geometric structure illustrated in FIG. 13A, showing straight outer struts and bent outer struts.
Figure 13E:
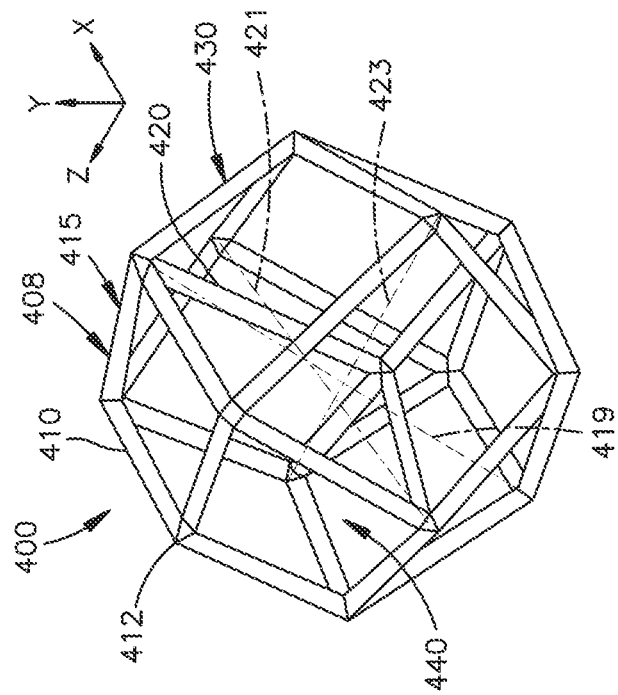
FIG. 13E is perspective view of the organic structure of FIG. 13D, showing all straight outer struts.
Figure 13D:
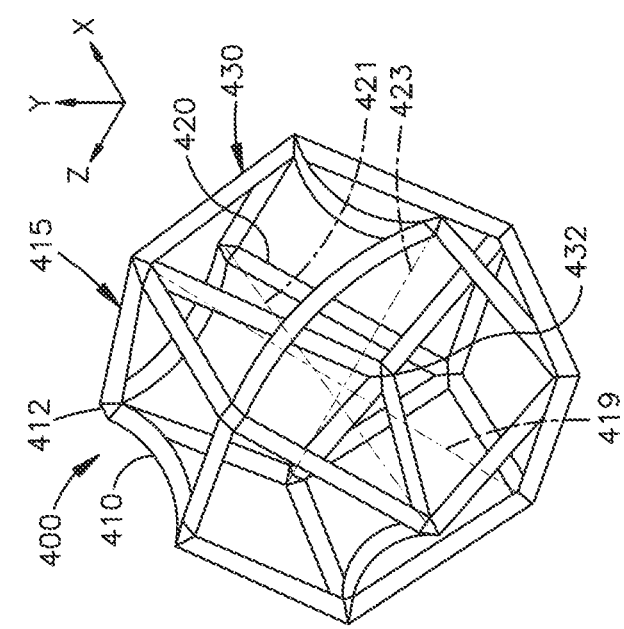
FIG. 13D is perspective view of an organic structure that is 50% modified with respect to the geometric structure illustrated in FIG. 13A, showing straight outer struts and bent outer struts.

Referring to FIGS. 13B-13C, the position of a given outer node 412 of the organic rhombic dodecahedron 415 is up to 25% modified with respect to the position of the corresponding outer node 212 of the geometric rhombic dodecahedron 215 as described above. In another embodiment illustrated in FIGS. 13D-13E, the position of a given outer node 412 of the organic rhombic dodecahedron 415 is up to 50% modified with respect to the position of the corresponding outer node 212 of the geometric rhombic dodecahedron 215 as described above. Further, in both FIGS. 13B and 13C, the struts 408 of the first organic structure 430 can include a plurality of internal struts 420 that, in combination with the outer struts 410, form a plurality of second organic structures 440 that are within the first organic structure 430. The internal struts 420 intersect each other so as to define an internal node 432 at an intersection of the internal struts. In particular, in the illustrative embodiment all of the internal struts 420 intersect each other to define the internal node 432. Further, each of the internal struts 420 extends from a respective different one of the plurality of outer nodes 412 to the internal node 432. In the illustrated embodiment, the internal struts 420 intersect each other so as to define only the single internal node 432 and no other internal nodes. Thus, the unit cell structure 400 defines only one single internal node 432 that is internal with respect to the outer nodes 412.

In the illustrative embodiment, the first organic structure 430 comprises the plurality of outer struts 410. As described above, the plurality of outer struts 410 cooperate to form the organic rhombic dodecahedron. Each second organic structure 440 is illustratively an organic trigonal trapezohedron. The plurality of organic second structures 440 within the organic first structure 430 include four organic trigonal trapezohedrons such that the unit cell structure 400 is an organic rhombic trigonal trapezohedron (ORTT). The organic trigonal trapezohedrons are modified with respect to the geometric trigonal trapezohedrons described above. For instance, at least one of the internal node 432 and at least one of the outer nodes 412 (including a plurality up to all of the outer nodes 412) is repositioned with respect to a corresponding at least one of the internal node and at least one of the outer nodes (including a plurality up to all of the outer nodes), respectively, of the geometric trigonal trapezohedrons described above. It will thus be appreciated that the resulting organic rhombic trigonal trapezohedron is modified with respect to the geometric rhombic trigonal trapezohedron described above. For instance, at least one of the internal node 432 and at least one of the outer nodes 412 (including a plurality up to all of the outer nodes 412) is repositioned with respect to a corresponding at least one of the internal node and at least one of the outer nodes (including a plurality up to all of the outer nodes), respectively, of the geometric rhombic trigonal trapezohedron described above.

Each second organic structure 440 is formed by a number of internal struts 420 and a number of outer struts 410. Each second organic structure 440 is illustratively an organic trigonal trapezohedron. As described above, the position of at least one or more of the outer nodes 412 up to all of the outer nodes 412 of the organic structure 430 are modified with respect to the outer nodes 212 of the second geometric structure 240. Further, the position of the internal node 432 of the second organic structure 440 is modified with respect to the position of the internal node 232 of the second geometric structure 240. In one illustrative embodiment shown in FIGS. 13B-13C, the position of at least one of the internal node 432 and at least one of the outer nodes 412 is modified up to 25% with respect to the position of the internal node 232 as illustrated in FIG. 3B-3C. In another illustrative embodiment shown in FIGS. 13D-13E, the position of at least one of the internal node 432 and at least one of the outer nodes 412 is modified up to 50% with respect to the position of the internal node 232 as illustrated in FIG. 3B-3C. As described above with respect to FIGS. 13B-13C, the first organic structure 430, the internal struts 420 of the second organic structure 440 of FIGS. 13D-13E intersect each other so as to define only the single internal node 432 and no other internal nodes. Thus, the unit cell structure 400 defines only one single internal node 432 that is internal with respect to the outer nodes 412.

With continuing reference to FIGS. 13B-13E, the first organic structure 430 includes the first, second, and third pairs of outer nodes 412 as described above with respect to FIGS. 12B-12C. Thus, the first straight imaginary line 419 extends through the first outer node 412a and the second outer node 412b. The second straight imaginary line 421 extends through the third outer node 412c and the fourth outer node 412d. The third straight imaginary line 423 extends through the fifth outer node 412e and the sixth outer node 412f. At least one or more up to all of the first straight imaginary line 419, the second straight imaginary line 421, and the third straight imaginary line 423 is offset from the internal node 232.

The organic unit cell structure 400 of FIGS. 13B-13E can be modified with respect to the geometric unit cell structure 200, such that the outer nodes 412 of the organic unit cell structure 400 are repositioned with respect to the corresponding outer nodes 212 of the geometric unit cell structure 200 in any suitable direction. Thus, outer nodes 412 of a first half of the organic unit cell structure 400 can be repositioned with respect to the corresponding outer nodes 212 of the geometric unit cell structure 200 in different directions. Similarly, the outer nodes 412 of a second half of the organic unit cell structure 400 can be repositioned with respect to the corresponding outer nodes 212 of the geometric unit cell structure 200 in different directions. The first and second halves of the organic unit cell structure 400 are separated from each other by a plane that bisects the organic unit cell structure 400, and the internal node 432 lies on the plane. Thus, in some examples, no matter the orientation of the plane (i.e., for all orientations of the plane), it is the case that at least some up to all of the outer nodes 412 of the first half of the organic unit cell structure 400 are repositioned with respect to the corresponding outer nodes 212 of the geometric unit cell structure 200 in different directions, and at least some up to all of the outer nodes 412 of the second half of the organic unit cell structure 400 are repositioned with respect to the corresponding outer nodes 212 of the geometric unit cell structure 200 in different directions.

As a result of the repositioned at least one node of the organic structure 430, at least one or more up to all of the internal struts 420 of the organic structure 430 have at least one property that is different than the corresponding internal struts 220 of the geometric structure 230. The property can include at least one of a length, orientation, and path type (e.g., straight or bent) of the internal strut 420. For instance, at least one or more of the internal struts 420 that partially define the repositioned internal node 432 can be longer or shorter than the corresponding internal struts 220 of the corresponding geometric structure 230. In this regard, the internal struts 420 extend from the respective outer node 412 to the internal node 432 along respective lengths, and the lengths of at least some of the internal struts 420 are different than each other. At least one or more up to all of the outer struts 410 of the organic outer structure 430 also have at least one geometric property that is different than the corresponding struts 210 of the geometric outer structure 230 as described above with respect to FIGS. 12B-C.

Further, the internal struts 420 shown in FIGS. 13B-13E can extend along any suitable path along its length from the respective outer node 412 to the internal node 432. For instance, or more of the internal struts 420 of the second organic structure 440 can extend along a straight and linear path along an entirety of its respective length, and can have a different orientation than the corresponding internal struts 220 of the second geometric structure 240. It is appreciated that all of the internal struts 420 illustrated in FIGS. 13B-13E can extend along respective straight paths from the respective outer node 412 to the internal node 432. Alternatively, at least a portion of at least one or more up to all of the internal struts 420 can be a bent internal strut along its length from the respective outer node 412 to the internal node 432. In one example, the at least a portion of the internal strut 420 can extend along a curved path. Alternatively or additionally, the at least a portion of at least one or more of the internal struts 420 can be angulated and thus bent. Alternatively, all of the internal struts 420 can be bent.

It has been found that the porous three-dimensional structure having the first organic structure 430 and the second organic structure 440 has a ductility that is greater than the ductility of the porous three-dimensional structure that includes the first geometric structure 230 and the second geometric structure 240. Further, the porous three-dimensional structure including the first organic structure 430 and the second organic structure 440 has suitable structural integrity when implanted in a human anatomy.

It should be appreciated that each unit cell structure may include other types of second organic structures. For example, an organic unit cell structure can include a plurality of outer struts 410 that defines the first organic structure 430 as described above. The modified unit cell structure can further include a plurality of internal struts 420 that, in combination with the outer struts 410, define a plurality of organic second or inner structures. Each of the organic inner structures can be configured as a modified octahedron. Thus, in one example, the organic unit cell structure can include eight internal struts 420 as described above with respect to FIG. 6. Accordingly, the plurality of second organic structures within the first organic structure can include six geometric octahedrons such that the organic unit cell structure is a modified or organic rhombic octahedron, whereby the position of at least some of the nodes of the first organic structure and at least some nodes of the second organic structure are repositioned with respect to the nodes of the first geometric structure and the nodes of the second geometric structure.

In one embodiment, the porous three-dimensional structure having the organic outer structure 430 and the organic inner structure 440 has a porosity from about 50% to about 75%. For instance, the porous three-dimensional structure having the organic outer structure 430 and the organic inner structure 440 can have a porosity from about 55% to about 65%. Further, as described above with respect to the geometric outer structures 230 and the geometric inner structures 240, the outer struts 410 and the internal struts 420 define a plurality of openings in the organic porous three-dimensional structure, each opening of the plurality of openings having a window size, and the internal volume of each organic structure 430 and 440 has a pore size. As described above, the pore size can be taken as the equivalent diameter of a sphere within the volume bounded within the unit cell having the organic structure 430.

Figure 14:
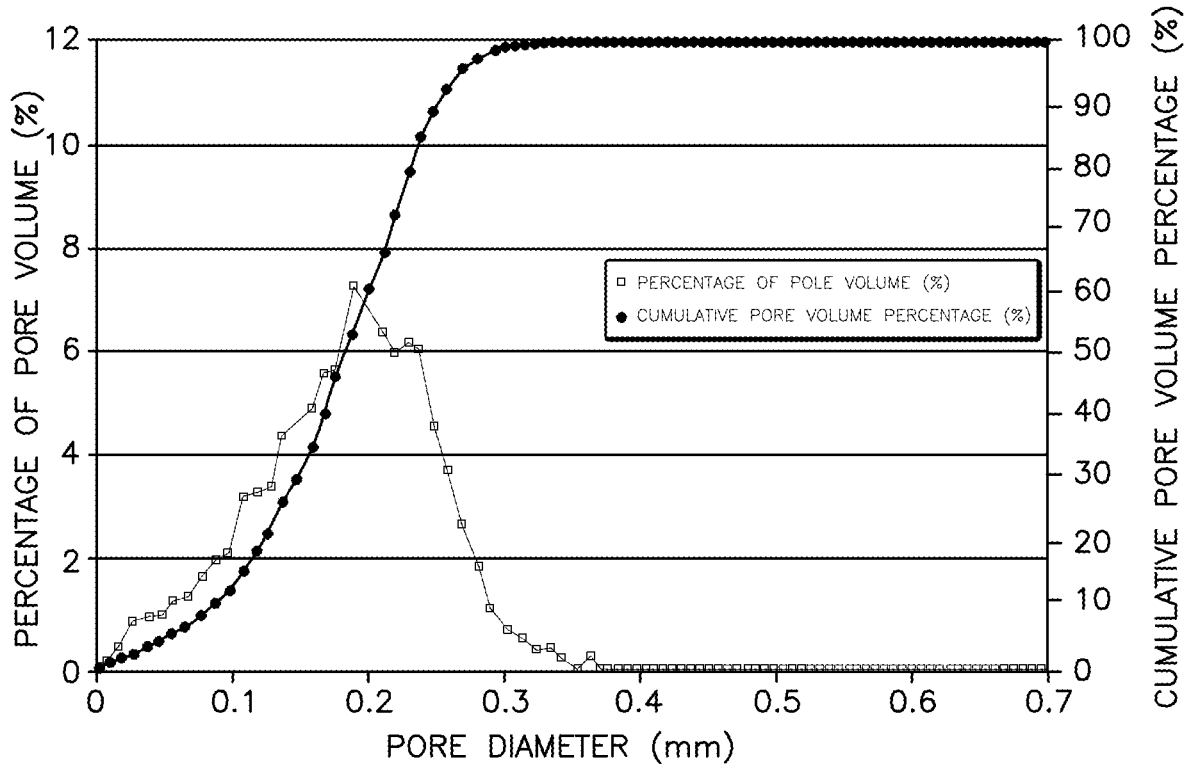
FIG. 14 illustrates a chart that plots the percentage of pores as a function of pore diameter for a porous three-dimensional structure having the unit cell geometry illustrated in FIG. 13C and a porosity of approximately 55%.

Referring to FIG. 14, the percentage of pores of the porous three-dimensional structure including the unit cells of FIG. 13C (e.g., ORTT with all struts 410 and 420 straight and linear), wherein the porous three-dimensional structure has a porosity of about 55%, and the positions of the nodes are 25% modified with respect to the GRTT. As illustrated, the percentage of pores of the three-dimensional structure having a pore diameter less than 0.1 mm is less than about 14.3 percent. For instance, less than about two percent of the pores have a pore size less than 0.1 mm. Further, FIG. 14 illustrates that approximately fifty percent of the pores of the three-dimensional structure have a pore diameter greater than 0.2 mm. For instance, approximately fifty percent of the pores of the three-dimensional structure have a pore diameter between approximately 0.2 mm and approximately 0.36 mm.

Figure 15:
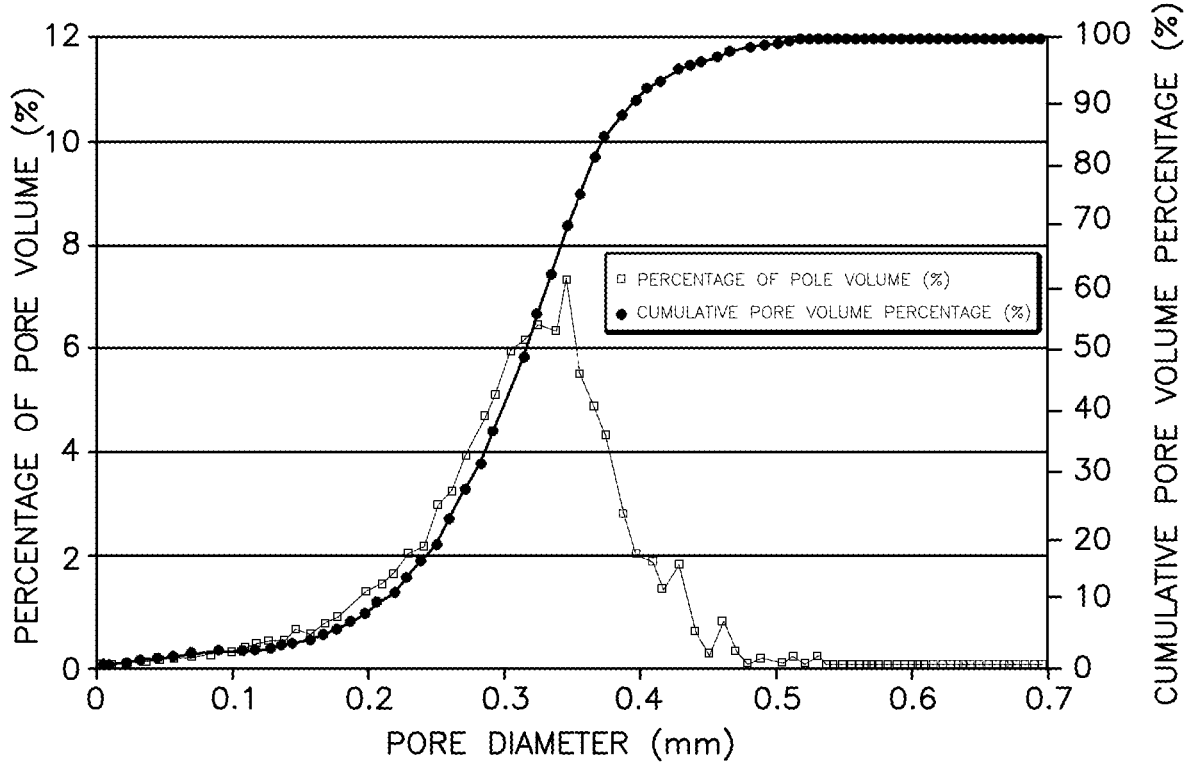
FIG. 15 illustrates a chart that plots the percentage of pores as a function of pore diameter for a porous three-dimensional structure having the unit cell geometry illustrated in FIG. 13C and a porosity of approximately 65%.

Referring to FIG. 15, the percentage of pores of the porous three-dimensional structure including the unit cells of FIG. 13C (e.g., ORTT with all struts 410 and 420 straight and linear), wherein the porous three-dimensional structure has a porosity of about 65%, and the position of at least one of the nodes is 25% modified with respect to the GRTT. As described above with respect to FIG. 14, the percentage of pores of the three-dimensional structure having a pore diameter less than 0.1 mm is less than about 14.3 percent. For instance, less than about 1.5 percent of the pores have a pore size less than 0.1 mm as illustrated in FIG. 15. Further, FIG. 15 illustrates that approximately fifty percent of the pores of the three-dimensional structure have a pore diameter greater than 0.3 mm. For instance, approximately fifty percent of the pores of the three-dimensional structure have a pore diameter between approximately 0.3 mm and approximately 0.7 mm. In particular approximately fifty percent of the pores of the three-dimensional structure have a pore diameter between approximately 0.3 mm and approximately 0.5 mm. It can be further ascertained from FIGS. 14-15 that approximately fifty percent of the pores of the three-dimensional structure having ORTT unit cells can have a pore diameter that ranges from approximately 0.2 mm to approximately 0.7 mm. For instance, approximately fifty percent of the pores of the three-dimensional structure having ORTT unit cells can have a pore diameter that ranges from approximately 0.2 mm to approximately 0.5 mm Further, as described above with respect to the geometric structures, the ratio of the pore size of the organic structures to the window size of each opening of the organic structures of a porous three-dimensional structure can be in a range of 1.00 to 2.90. It is recognized in some examples that at least ninety percent of the organic structures have the ratio of the pore size to the window size of each opening in the range of 1.00 to 2.90. For instance, as described above with respect to the geometric structures, in one embodiment, the ratio of the pore size of each organic structure to the window size of each opening of the organic structure is in a range of 1.00 to 1.10. It is recognized in some examples that at least ninety percent of the organic structures have the ratio of the pore size to window size of each opening in the range of 1.00 to 2.90. In another example, as described above with respect to the porous three-dimensional structure having the geometric unit cells, the ratio of the pore size of an organic unit cell to any of its corresponding window sizes is in a range of 1.50 to 1.60. It is recognized in some examples that at least ninety percent of the organic unit cells can have the ratio of the pore size to any of its corresponding window sizes in the range of 1.50 to 2.60.

Referring again to FIGS. 12A-13E generally, methods are provided for designing the unit cells described herein, having one or both of the first and second porous organic three-dimensional structures configured to encourage bone ingrowth when implanted in a human body. The method can include the step of applying a modification factor to a first geometric unit cell design. The first geometric unit cell design includes a number of first or outer struts 210, sch as three outer struts 210, that intersect each other so as to define a number of first or outer nodes 212, wherein each of the first struts 210 has a respective first length, and the first nodes 212 define a first relative position with respect to each other. The respective first lengths of the first struts 210 are all substantially equal to each other in one embodiment. In another embodiment, the respective first lengths of some of the first struts are different than the respective first lengths of at least some others of the first struts 210. The first unit cell design can be provided in the manner described above. The modification factor can be up to 50%, such as up to 25% in the manner described above. In one example, the applying step can be performed using a 3-matic software package commercially available from Materialise having a place of business in Leuven, Belgium.

The applying step produces a second unit cell design having a number of second or outer struts 410 that intersect each other so as to define a number of second or outer nodes 412. The number of outer nodes 412 equals the number of outer nodes 212, and the number of outer struts 410 equals the number of outer struts 210. Each of the outer struts 410 has a respective first length, and the outer nodes 412 define a second relative position with respect to each other that is different than the first relative position. The respective first lengths of at least some of the outer struts 410 are different than the respective first lengths of at least some others of the outer struts 410. Further, the respective first lengths of at least some of the outer struts 410 are different than the respective first lengths of at least some of the corresponding outer struts 210. Alternatively, the organic three-dimensional structures 430 and 440 can be designed without the aid of a previously-designed geometric structures 230 and 240, respectively. It is recognized that manufacturing tolerances can result in different strut lengths. However, different strut lengths as described herein refers to different lengths outside of manufacturing tolerances.

Once the second unit cell design has been produced, manufacturing instructions can be generated to fabricate the porous three-dimensional structure including a plurality of interconnected unit cells each having the second unit cell design. The porous three-dimensional structure can be manufactured on-site. Alternatively, the manufacturing instructions can be sent to a third party manufacturer to fabricate the porous three-dimensional structure.

In accordance with various embodiments, an orthopaedic implant is provided. The implant can include a porous three-dimensional structure comprising a plurality of unit cells. Each unit cell can comprise an outer geometric structure having a first geometry and comprising a plurality of first struts. Each unit cell can further comprise an inner geometric structure having a second geometry and further comprise a plurality of second struts connected to a portion of the plurality of first struts to form the inner geometric structure within the outer geometric structure.

In accordance with various embodiments, the outer geometric structure can be a rhombic dodecahedron. The inner geometric structure can be a trigonal trapezohedron. The trigonal trapezohedron can be formed by inserting four struts into the outer geometric structure. Further, the at least one unit cell can include four trigonal trapezohedron geometric structures within the outer geometric structure.

As described above, an orthopaedic implant can include a porous three-dimensional structure comprising a plurality of repeating unit cells having unit cell structures. The unit cell structures can define geometric or organic geometric structures. Accordingly, it is recognized that the porous three-dimensional structure can include a plurality of groups of outer struts that define respective first geometric or organic structures. Further, some of the unit cell structures can be surrounded by, or otherwise disposed inward with respect to, other unit cell structures of the porous three-dimensional structure of the orthopaedic implant. As a result, when the unit cell structures are combined to define the porous three dimensional structure, the outer struts of certain unit cell structures can define outer struts of adjacent unit cell structures. Further, when the unit cell structures include inner struts that define second geometric or organic structures, it is recognized that the inner struts of certain unit cell structures can define outer struts of adjacent unit cell structures. Conversely, the outer struts of certain unit cell structures can define inner structs of adjacent unit cell structures. Therefore, any suitable combination of struts in the porous three-dimensional structure of the orthopaedic implant can define outer struts of the type described herein irrespective of whether other struts exist that are disposed outward from the outer struts or extend from the outer struts. Similarly, any suitable combination of struts in the porous three-dimensional structure of the orthopaedic implant can define inner struts of the type described herein that extend from the respective outer struts to an inner node. In some examples, the unit cell structures can consist or consist essentially of the outer struts that define the outer nodes. In other examples, the unit cell structures can consist or consist essentially of the outer struts that define the outer nodes, and the inner struts that define the inner node.

Manufacturing Processes

The porous three-dimensional metallic structures disclosed above can be made using a variety of different additive manufacturing techniques. For instance, in accordance with various embodiments, a method for producing the porous three-dimensional structure 120 comprises depositing and scanning successive layers of metal powders with a beam. The beam (or scanning beam) can be an electron beam. The beam (or scanning beam) can be a laser beam.

Regarding the various methods described herein, the metal powders can be sintered to form the porous three-dimensional structure. Alternatively, the metal powders can be melted to form the porous three-dimensional structure. The successive layers of metal powders can be deposited onto a solid base (see above for discussion regarding base). In various embodiments, the types of metal powders that can be used include, but are not limited to, titanium, titanium alloys, stainless steel, cobalt chrome alloys, tantalum or niobium powders.

Regarding the various methods described herein, the geometric properties can be selected from the group consisting of, porosity, pore size, minimum opening size, and combinations thereof. The porosity can be between about 20% and about 95%. The porosity can also be between about 40% and about 80%. The porosity can also be between about 50% and about 75%. Moreover, strut lengths can be modified to be about 25% to about 175% of the average strut length of the plurality of struts. The individual outer strut lengths can also be modified to be, for example, about 50% to about 150% of the average strut length of the plurality of outer struts. The individual outer strut lengths can also be modified to be, for example, about 75% to about 125% of the average strut length of the plurality of outer struts. Further, the unit cell can have a pore size less than the first geometric structure pore size. Moreover, the unit cell can have a window size greater than the window size of each of the plurality of second geometric structures.

Regarding the various methods described, the first geometric structure can be a rhombic dodecahedron. Each of the second geometric structures can be a trigonal trapezohedron. The trigonal trapezohedron can be formed by inserting four struts into the first geometric structure. Further, the at least one unit cell can include four trigonal trapezohedron geometric structures within the first geometric structure.

In various embodiments, a method for producing a porous three-dimensional structure is provided, the method comprising applying a stream of metal particles at a predetermined velocity onto a base to form a porous three-dimensional structure comprising a plurality of unit cells and having predetermined geometric properties, each unit cell comprising a plurality of outer struts and a plurality of internal struts. Each unit cell can include, a first geometric structure comprising the plurality of outer struts, and a plurality of second geometric structures, formed out of the plurality of internal struts within the first geometric structure. In various embodiments, the types of metal particles that can be used include, but are not limited to, titanium, titanium alloys, stainless steel, cobalt chrome alloys, tantalum or niobium particles.

The predetermined velocity can be a critical velocity required for the metal particles to bond upon impacting the base. The critical velocity is greater than 340 m/s.

The method can further include applying a laser at a predetermined power setting onto an area of the base where the stream of metal particles is impacting The first geometric structure can be a rhombic dodecahedron. In some embodiments, each of the second geometric structures can be a trigonal trapezohedron. That is, four trigonal trapezohedrons can be formed by inserting four struts into the first geometric structure. In some embodiments, octahedrons can be formed, for example, by inserting eight internal struts into a first geometric structure. In this case, six octahedron geometric structures can be provided within the first geometric structure.

In accordance with various embodiments, a method for producing a porous three-dimensional structure is provided, the method comprising introducing a continuous feed of metal wire onto a base surface and applying a beam at a predetermined power setting to an area where the metal wire contacts the base surface to form a porous three-dimensional structure comprising a plurality of unit cells and having predetermined geometric properties. Each unit cell can comprise a plurality of outer struts and a plurality of internal struts, each unit cell including a first geometric structure comprising the plurality of outer struts, and a plurality of second geometric structures, formed out of the plurality of internal struts within the first geometric structure. The beam (or scanning beam) can be an electron beam. The beam (or scanning beam) can be a laser beam. In various embodiments, the types of metal wire that can be used include, but are not limited to, titanium, titanium alloys, stainless steel, cobalt chrome alloys, tantalum or niobium wire.

The first geometric structure can be a rhombic dodecahedron. In some embodiments, each of the second geometric structures can be a trigonal trapezohedron. That is, four trigonal trapezohedrons can be formed by inserting four struts into the first geometric structure. In some embodiments, octahedrons can be formed, for example, by inserting eight internal struts into a first geometric structure. That is, six octahedron geometric structures can be provided within the first geometric structure.

In accordance with various embodiments, a method for producing a porous three-dimensional structure is provided, the method comprising introducing a continuous feed of a polymer material embedded with metal elements onto a base surface. The method can further comprise applying heat to an area where the polymer material contacts the base surface to form a porous three-dimensional structure comprising a plurality of unit cells and having predetermined geometric properties. Each unit cell can comprise a plurality of outer struts and a plurality of internal struts. Each unit cell includes a first geometric structure comprising the plurality of outer struts, and a plurality of second geometric structures, formed out of a number of the internal struts within the first geometric structure and a number of outer struts. The metal elements can be a metal powder. In various embodiments, the continuous feed of the polymer material can be supplied through a heated nozzle thus eliminating the need to apply heat to the area where the polymer material contacts the base surface to form the porous three-dimensional structure. In various embodiments, the types of metal elements that can be used to embed the polymer material can include, but are not limited to, titanium, titanium alloys, stainless steel, cobalt chrome alloys, tantalum or niobium.

The method can further comprise scanning the porous three-dimensional structure with a beam to burn off the polymer material. The beam (or scanning beam) can be an electron beam. The beam (or scanning beam) can be a laser beam.

The first geometric structure can be a rhombic dodecahedron. In various embodiments, each of the second geometric structures can be a trigonal trapezohedron. That is, four trigonal trapezohedrons can be formed by inserting four struts into the first geometric structure. In various embodiments, octahedrons can be formed, for example, by inserting eight internal struts into a first geometric structure. That is, six octahedron geometric structures can be provided within the first geometric structure.

In accordance with various embodiments, a method for producing a porous three-dimensional structure is provided, the method comprising introducing a metal slurry through a nozzle onto a base surface to form a porous three-dimensional structure comprising a plurality of unit cells and having predetermined geometric properties. Each unit cell can comprise a plurality of outer struts and a plurality of internal struts. Each unit cell can include a first geometric structure comprising the plurality of outer struts, and a plurality of second geometric structures, formed out of a number of the internal struts within the first geometric structure and a number of the outer struts. In various embodiments, the nozzle is heated at a temperature required to bond metallic elements of the metal slurry to the base surface. In various embodiments, the metal slurry is an aqueous suspension containing metal particles along with one or more additives (liquid or solid) to improve the performance of the manufacturing process or the porous three-dimensional structure. In various embodiments, the metal slurry is an organic solvent suspension containing metal particles along with one or more additives (liquid or solid) to improve the performance of the manufacturing process or the porous three-dimensional structure. In various embodiments, the types of metal particles that can be utilized in the metal slurry include, but are not limited to, titanium, titanium alloys, stainless steel, cobalt chrome alloys, tantalum or niobium particles.

The first geometric structure can be a rhombic dodecahedron. In some embodiments, each of the second geometric structures can be a trigonal trapezohedron. That is, four trigonal trapezohedrons can be formed by inserting four struts into the first geometric structure. In various embodiments, octahedrons can be formed, for example, by inserting eight internal struts into a first geometric structure. That is six octahedron geometric structures can be provided within the first geometric structure.

In accordance with various embodiments, a method for producing a porous three-dimensional structure is provided, the method comprising introducing successive layers of molten metal onto a base surface to form a porous three-dimensional structure comprising a plurality of unit cells and having predetermined geometric properties. Each unit cell can comprise a plurality of outer struts and a plurality of internal struts. Each unit cell can include a first geometric structure comprising the plurality of outer struts, and a plurality of second geometric structures, formed out of the plurality of internal struts within the first geometric structure and a number of the outer struts. Further, the molten metal can be introduced as a continuous stream onto the base surface. The molten metal can also be introduced as a stream of discrete molten metal droplets onto the base surface. In various embodiments, the types of molten metals that can be used include, but are not limited to, titanium, titanium alloys, stainless steel, cobalt chrome alloys, tantalum or niobium.

The first geometric structure can be a rhombic dodecahedron. In various embodiments, each of the second geometric structures can be a trigonal trapezohedron. That is, four trigonal trapezohedrons can be formed by inserting four struts into the first geometric structure. In various embodiments, octahedrons can be formed, for example, by inserting eight internal struts into a first geometric structure. That is, six octahedron geometric structures can be provided within the first geometric structure.

In accordance with various embodiments, a method for producing a porous three-dimensional structure is provided, the method comprising applying and photoactivating successive layers of photosensitive polymer embedded with metal elements onto a base surface to form a porous three-dimensional structure comprising a plurality of unit cells and having predetermined geometric properties. Each unit cell can comprise a plurality of outer struts and a plurality of internal struts. Each unit cell can include a first geometric structure comprising the plurality of outer struts, and a plurality of second geometric structures, formed out of the plurality of internal struts within the first geometric structure and a number of the outer struts. In various embodiments, the types of metal elements that can be used to embed the polymer material can include, but are not limited to, titanium, titanium alloys, stainless steel, cobalt chrome alloys, tantalum or niobium.

The first geometric structure can be a rhombic dodecahedron. In some embodiments, each of the second geometric structures can be a trigonal trapezohedron. That is, four trigonal trapezohedrons can be formed by inserting four struts into the first geometric structure. In some embodiments, octahedrons can be formed, for example, by inserting eight internal struts into a first geometric structure. That is, six octahedron geometric structures can be provided within the first geometric structure.

In accordance with various embodiments, a method for producing a porous three-dimensional structure is provided, the method comprising depositing and binding successive layers of metal powders with a binder material to form a porous three-dimensional structure comprising a plurality of unit cells and having predetermined geometric properties. Each unit cell can comprise a plurality of outer struts and a plurality of internal struts. Each unit cell can include a first geometric structure comprising the plurality of outer struts, and a plurality of second geometric structures, formed out of the plurality of internal struts within the first geometric structure and a number of the outer struts. In various embodiments, the types of metal powders that can be used include, but are not limited to, titanium, titanium alloys, stainless steel, cobalt chrome alloys, tantalum or niobium powders.

The method can further include sintering the bound metal powder with a beam. The beam (or scanning beam) can be an electron beam. The beam (or scanning beam) can be a laser beam.

The method can further include melting the bound metal powder with a beam. The beam (or scanning beam) can be an electron beam. The beam (or scanning beam) can be a laser beam.

The first geometric structure can be a rhombic dodecahedron. In some embodiments, each of the second geometric structures can be a trigonal trapezohedron. That is, four trigonal trapezohedrons can be formed by inserting four struts into the first geometric structure. In some embodiments, octahedrons can also be formed, for example, by inserting eight internal struts into a first geometric structure. That is, six octahedron geometric structures can be provided within the first geometric structure.

In accordance with various embodiments, a method for producing a porous three-dimensional structure is provided, the method comprising depositing droplets of a metal material onto a base surface, and applying heat to an area where the metal material contacts the base surface to form a porous three-dimensional structure comprising a plurality of unit cells and having predetermined geometric properties. Each unit cell can comprise a plurality of outer struts and a plurality of internal struts. Each unit cell can include a first geometric structure comprising the plurality of outer struts, and a plurality of second geometric structures, formed out of the plurality of internal struts within the first geometric structure and a number of the outer struts. The beam (or scanning beam) can be an electron beam. The beam (or scanning beam) can be a laser beam. In various embodiments, the types of metal materials that can be used include, but are not limited to, titanium, titanium alloys, stainless steel, cobalt chrome alloys, tantalum or niobium.

The deposited droplets of metal material can be a metal slurry embedded with metallic elements. The metal material can be a metal powder.

The first geometric structure can be a rhombic dodecahedron. In some embodiments, each of the second geometric structures can be a trigonal trapezohedron. That is, four trigonal trapezohedrons can be formed by inserting four struts into the first geometric structure. In some embodiments, octahedrons can be formed, for example, by inserting eight internal struts into a first geometric structure. That is, six octahedron geometric structures can be provided within the first geometric structure.

Although specific embodiments and applications of the same have been described in this specification, these embodiments and applications are exemplary only, and many variations are possible.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed:

1. An implantable apparatus, comprising:
   a porous three-dimensional structure shaped to be implanted in a patient's body, the porous three-dimensional structure including a plurality of interconnected organic unit cells, each organic unit cell including:
      a plurality of outer struts, wherein respective groups of outer struts intersect so as to define a respective plurality of outer nodes, and wherein the plurality of outer struts combine to define a lattice structure; and
      a plurality of internal struts, each internal strut extending from a different respective one of the outer nodes, and the internal struts intersect so as to define an internal node,
   wherein the plurality of outer nodes includes a first outer node defined by the intersection of a first group of outer struts and a second outer node defined by the intersection of a second group of outer struts, wherein the second outer node is opposite the first outer node such that the first and second outer nodes are spaced further from each other than from any other outer node, wherein a shortest path along the outer struts from the first outer node to the second outer node includes only three intermediate outer nodes of the plurality of outer nodes, wherein all outer struts that extend to the three intermediate outer nodes are configured such that the three intermediate outer nodes define respective vertices, and
   wherein a straight imaginary line extends through the first outer node and the second outer node, and the internal node is offset from the straight imaginary line.

2. The implantable apparatus of claim 1, wherein each of the outer struts has a constant thickness along an entirety of its length.

3. The implantable apparatus of claim 1, wherein each of the internal struts has a constant thickness along an entirety of its length.

4. The implantable apparatus of claim 1, wherein at least one of the outer struts is curved along its length.

5. The implantable apparatus of claim 1, wherein at least one of the internal struts is curved along its length.

6. The implantable apparatus of claim 1, wherein all of the outer struts extend from and to a respective pair of the outer nodes along respective lengths, and the lengths of at least some of the outer struts are different than each other.

7. The implantable apparatus of claim 1, wherein all of the internal struts and outer struts are substantially straight along entireties of their respective lengths.

8. The implantable apparatus of claim 1, having a porosity between about 50% and about 75%.

9. The implantable apparatus of claim 1, comprising a number of pores defined by the unit cells, respectively, wherein less than 14.3 percent of the pores have a pore size less than 0.1 mm.

10. The implantable apparatus of claim 9, wherein fifty percent of the pores have a pore size that ranges from approximately 0.2 mm to approximately 0.7 mm.

11. The implantable apparatus of claim 10, wherein the outer struts cooperate to define a number of outer openings, the internal struts cooperate with a number of the outer struts to form number of internal openings, the porous three-dimensional structure defines window sizes defined as a diameter of a circle positioned in the corresponding outer openings and inner openings, such that each of the struts that defines the outer openings and inner openings, respectively, is positioned on a tangent line of the circle, and the implantable apparatus comprises a number of pores defined by the unit cells, respectively, the pores defining a ratio of their respective pore sizes to any of its window sizes that is in the range of 1.00 to 2.90.

12. The implantable apparatus of claim 1, wherein the internal node is the only internal node of the porous three-dimensional structure that is internal with respect to the outer nodes.

13. The implantable apparatus of claim 1, wherein all of the internal struts intersect at the internal node.

14. The implantable apparatus of claim 1, wherein each organic unit cell defines a first half and a second half separated from the first half by a plane that bisects the organic unit cell, and for all orientations of the plane, 1) at least some of the outer nodes of the first half of the organic unit cell are repositioned in a first direction with respect to corresponding outer nodes of a corresponding reference geometric unit cell, and 2) at least some of the outer nodes of the second half of the organic unit cell are repositioned in a second direction with respect to corresponding outer nodes of the corresponding reference geometric unit cell, wherein the second direction is different than the first direction.

15. The implantable apparatus of claim 1, further comprising an organic rhombic trigonal trapezohedron having a ductility greater than a corresponding reference geometric rhombic trigonal trapezohedron.

16. The implantable apparatus of claim 1, further comprising a solid base, wherein the porous three-dimensional structure is attached to the solid base.

17. The implantable apparatus of claim 1, wherein all opposed outer nodes are separated by each other by only three intermediate outer nodes of the plurality of outer nodes along a shortest path along the outer struts, and the nodes of pairs of opposed outer nodes are spaced further from each other than from any other node.

18. The implantable apparatus of claim 1, wherein the internal node of each organic unit cell is the only internal node of each organic unit cell that is disposed within the lattice structure.

* * * * *